United States Patent
Ozturk et al.

(10) Patent No.: US 10,472,373 B2
(45) Date of Patent: Nov. 12, 2019

(54) THIENOTHIOPHENE/ DITHIENOTHIOPHENE-TRIPHENYLAMINE/ TETRAPHENYLETHYLENE DERIVATIVES FOR ORGANIC LIGHT EMITTING DIODES

(71) Applicant: TUBITAK

(72) Inventors: Turan Ozturk, Istanbul (TR); Ali Buyruk, Istanbul (TR); Emine Tekin, Kocaeli (TR); Selin Piravadili Mucur, Kocaeli (TR); Ahmet Ceyhan Goren, Kocaeli (TR)

(73) Assignee: TUBITAK, Ankara (TR)

( * ) Notice: Subject to any disclaimer, the term of this patent is extended or adjusted under 35 U.S.C. 154(b) by 0 days.

(21) Appl. No.: 15/552,491

(22) PCT Filed: Feb. 20, 2015

(86) PCT No.: PCT/IB2015/051305
§ 371 (c)(1),
(2) Date: Aug. 21, 2017

(87) PCT Pub. No.: WO2016/132179
PCT Pub. Date: Aug. 25, 2016

(65) Prior Publication Data
US 2018/0093996 A1 Apr. 5, 2018

(51) Int. Cl.
| | | |
|---|---|---|
| C07D 495/04 | (2006.01) |
| H01L 51/00 | (2006.01) |
| C07D 495/14 | (2006.01) |
| C09K 11/06 | (2006.01) |
| H01L 51/50 | (2006.01) |

(52) U.S. Cl.
CPC ......... *C07D 495/04* (2013.01); *C07D 495/14* (2013.01); *C09K 11/06* (2013.01); *H01L 51/0074* (2013.01); *C09K 2211/1092* (2013.01); *H01L 51/5012* (2013.01)

(58) Field of Classification Search
CPC .... C07D 495/04; C07D 495/14; C09K 11/06; C09K 2211/1092; H01L 51/0074; H01L 51/5012
USPC .......................................................... 252/500
See application file for complete search history.

(56) References Cited

U.S. PATENT DOCUMENTS

2015/0280133 A1* 10/2015 Parham ................ C07D 413/14
257/40

FOREIGN PATENT DOCUMENTS

WO    2014067614 A1    5/2014

OTHER PUBLICATIONS

Dong Yongqiang et al: "Aggregation-induced emissions of tetraphenylethene derivatives and their utilities as chemical vapor sensors and in organic light-emitting diodes", Applied Physics Letters, vol. 91, No. 1, Jul. 5, 2007 (Jul. 5, 2007), pp. 011111-1 to 011111-3, XP012098927, American Institute of Physics, US; ISSN: 0003-6951, DOI: 10.1063/1.2753723.

* cited by examiner

*Primary Examiner* — Harold Y Pyon
*Assistant Examiner* — Danny N Kang
(74) *Attorney, Agent, or Firm* — AEON Law, PLLC; Adam L. K. Philipp; Martin S. Garthwaite

(57) ABSTRACT

The present invention discloses new molecules having defined structures of a series of thienothiophene (TT), dithienothiophene (DTT) and their substituted derivatives with triphenylamine and tetraphenylethylene, light emitting devices of which are expected to be applied to organic light emitting diodes (OLED).

15 Claims, 3 Drawing Sheets

THIENOTHIOPHENE/ DITHIENOTHIOPHENE-TRIPHENYLAMINE/ TETRAPHENYLETHYLENE DERIVATIVES FOR ORGANIC LIGHT EMITTING DIODES

FIELD OF INVENTION

The present invention relates to thienothiophene, dithienothiophene and their triphenylamine, tetraphenylethylene and their various compositions with specified structures. They have potential of application to organic light emitting diodes (OLED).

BACKGROUND OF THE INVENTION

Organic electronic and optoelectronic materials have been attracting the attention of growing number of researchers for more than 50 years. The design and synthesis of new π-conjugated organic materials, displaying better properties is one of the most investigated subjects. Properties of the organic materials could directly be affected through the modification of the chemical structures of organic compounds Until the mid-1980s, stability and performance of the devices made of organic materials fell short of those devices based on materials such as silicon or gallium arsenide, which was changed with the appearance of a low voltage and efficient thin film light emitting diode. It provided the possibility of using organic thin films for a new generation of electronic and optoelectronic devices. It has now been proven that organic thin films are useful in various applications and organic light emitting device (OLED) is the most successful one, which is used now m full-color displays.

Generally, two groups of organic materials, small molecules and polymers, are used in electronic and optoelectronic devices and allow low cost fabrication of devices (C W. Tang, Appl Phys Letters. 1987, 51, 913-915; J. H. Burroughes, Nature. 1990, 347, 539; U.S. Pat. Nos. 6,727, 008, 7,133,032. WO 2007/134280A1; US2005/01184A1; WO9/13148; US005399502; U.S. Pat. No. 4,356,429).

Designing high performance optical and electronic organic devices requires understanding of their electronic structures and even some small tunings in the structure or composition of an organic material can after its original properties enormously. Modification of the structures of the conjugated organic materials to tune their optoelectronic properties is a challenging topic. On the other hand, conjugated polymers pose some problems like reproducibility, purification, and hence electronic properties. Moreover, extra performance might be required to separate of the materials containing conjugated chains of various lengths in order to decrease polydispersity In some cases, to remove the remnant terminal groups by appropriate chemical treatment could be necessary. These extra performances contribute to the increase of the cost and environmental impact of the material. As an alternative, small and soluble conjugated organic molecules could be used in optical and electronic organic devices. Due to their reproducible syntheses and better purification, organic molecules provide more direct and reliable analyses of structure—property relationships, which are the crucial points for high performance organic molecules used in devices.

Thiophene-based organic materials are among the most promising compounds with tunable functional properties by proper molecular engineering Such tuning can also be performed by using fused thienothiophene (TT), dithienothiophene (DTT) as their core skeleton consist of two and more fused rigid thiophene rings and create better π-conjugation and π-π stacking in their solid states to enhance their hole-electron mobility (Skabara, P. J. In Handbook of Thiophene-based Materials; Perepichka, I. F., Perepichka, D. F., Eds.; John Wiley & Sons: Chichester, U.K., 2009; Chapter 3 and Comel, A.; Sommen. G, Kirsch. G. Mini-Rev Org. Chem. 2004, 1, 367-374).

To achieve a substantial breakthrough, design of stable and efficient organic π-conjugated materials with better optical and electronic properties is particularly important. In spite of many luminescent materials exhibiting strong photoluminescence in dilute solutions, their light emission in concentrated solutions or in the solid state are often weakened or almost quenched due to strong π-π stacking, which is known as AIQ, Aggregation Induced Quenching, (T. Forster and K. Kasper, Z. Phys. Chem., 1954, 1, 275 and A. C. Grimslale, K. L. Chan, R E Martin. P G. Jokisz and A. B Holmes, Chem Rev, 2009, 109, 897). On the other hand, Tang and co-workers introduced a new alternative concept, Aggregation-Induced Emission (AIE), which is exactly opposite to AIQ. Organic material emits strong light particularly in its solid or aggregation states. (J. Luo. Z. Xie, J. W. Y Lam, L. Cheng, H. Chen, C. Qiu, H. S. Kwok, X. Zhan, Y. Liu, D Zhu and B. 2 Tang, Chem. Commun., 2001, 1740 and Z. Zhao, Z. Wang, P. Lu, C. Y. K. Chan, D. Liu, J. W. Y. Lam. H. H. Y. Sung, I. D. Williams, Y. Ma and B. Z Tang. Angew. Chem., Int. Ed., 2009, 48, 7608). Tetraphenylethene (TPE), with its simpler molecular structure, is counted among the most effective molecule producing AIE (Y. Dong, J. W. Y. Lam, A. Qin, J. Liu, Z. Li, B. Z. Tang, J. Sun and H. S. Kwok, Appl. Phys. Lett., 2007, 91, 011111). The AIE nature and hole-transport capability of a material, having tetraphenylethylene and Iriphenylamine, have enabled the fabrication of OLEDs devices with simple structures, low-cost and very good performance (Tang Z. B. Adv. Mater. 2010, 22, 19). Thus, it would be desirable developing materials having emissive and hole-transporting multiple functional abilities for organic light emitting diodes. Due to multiple functional properties of these molecules, simple device structures with no extra hole-transporting materials) in order to reduce the fabrication cost, could be fabricated.

DISCLOSURE OF THE INVENTION

The invention discloses the compounds having the formulas (I)-(X), (XI)-(XXX), (XXXI)-(L), (LI)-(LIV), (LV)-(LXII), (LXIII)-(LXX), (LXXI)-(LXXIV), (LXXV)-(LXXXII) and (LXXXIII)-(XC).

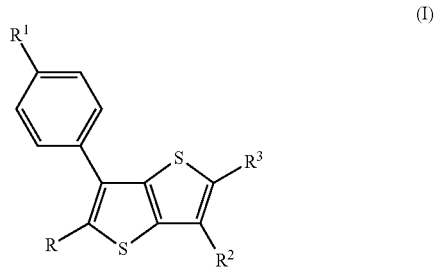

(I)

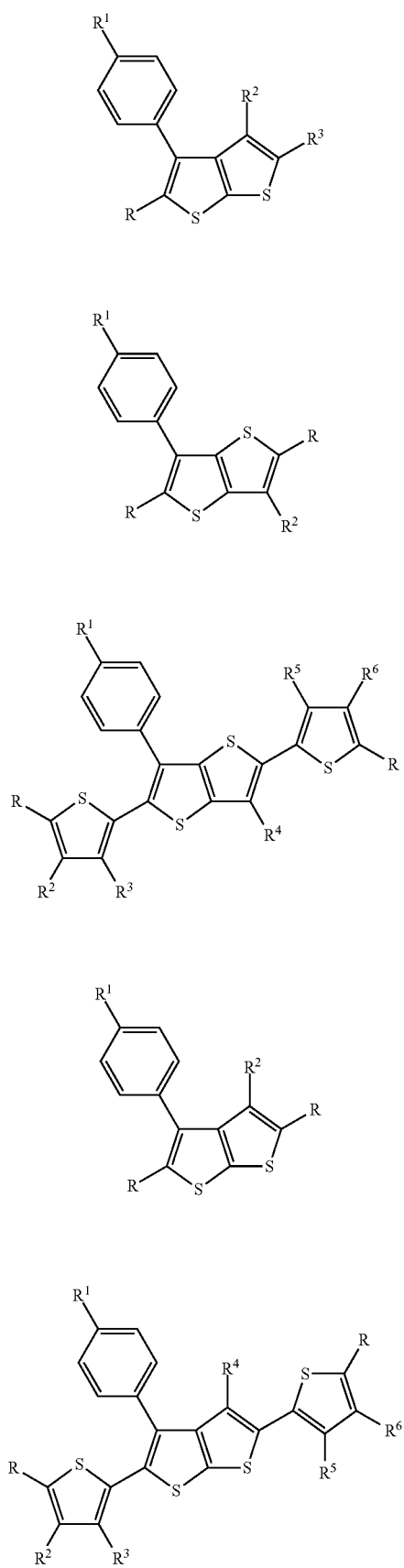
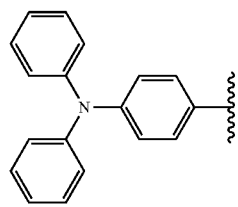
R¹ = —H, —OCH₃, —NO₂, —NH₃, —N(CH₃)₂, —CN

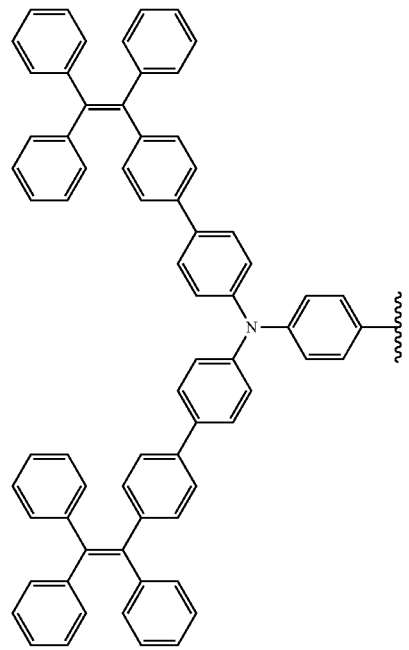
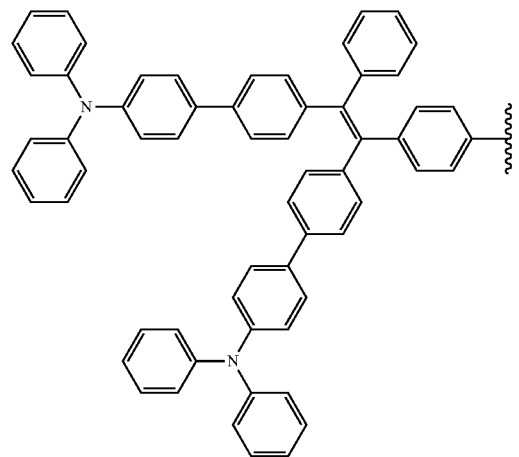
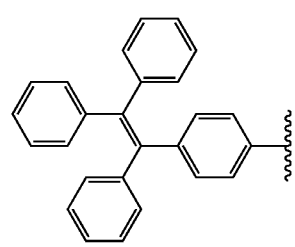
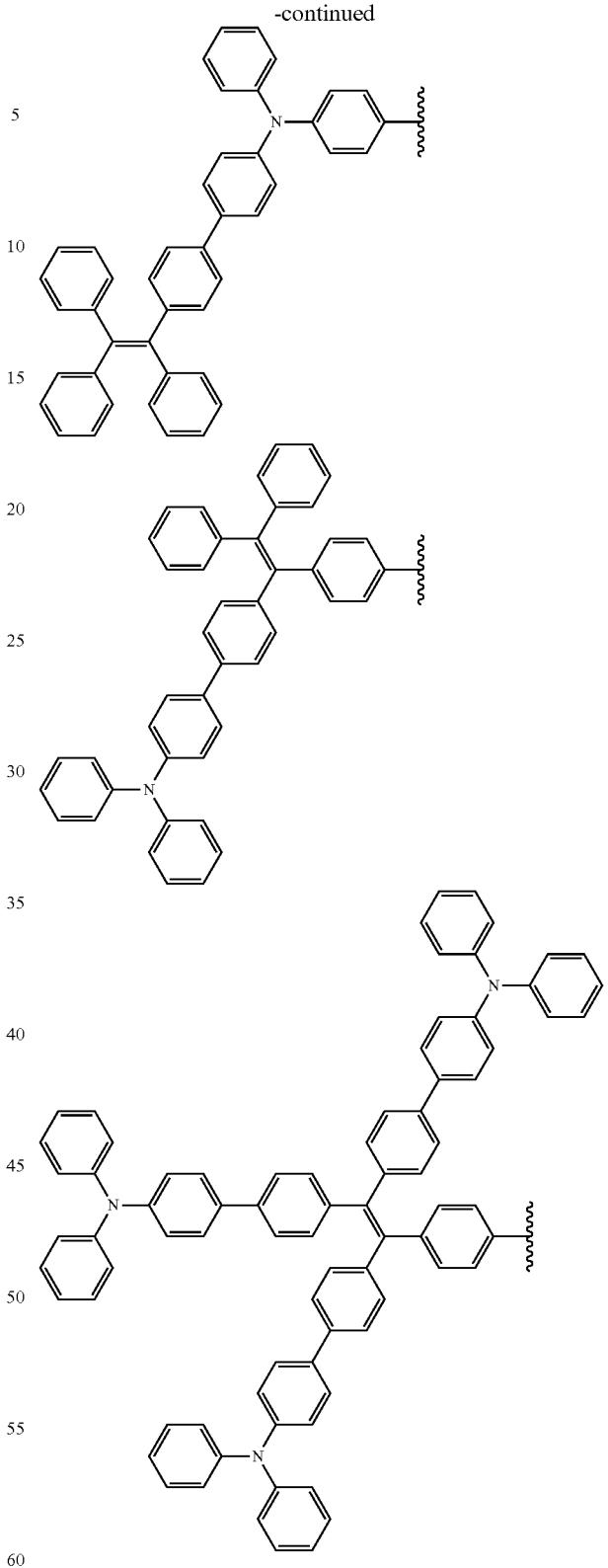
WO 2014/067614 A1 discloses dithienothiophene-triphenylamine derivatives for use as active compounds in OLEDs. The present compounds differ from the structurally closest compounds in WO 2014/067614 A1 (D1: e.g. page 82, compound 7s; page 86, compound 8k) in the substituent R. WO 2014/067614 A1 does not disclose or suggest any compounds wherein the triphenylamine group is unsubstituted or substituted by a tetraphenylethylene group. In WO 2014/067614 A1 the corresponding triphenylamine group is p-phenyl substituted and/or fused so as to form an benzoindene tricycle. Also in the present compounds the triphenylamine group is always separated by a phenyl or a thiophene if in 2-position of the thienothiophene. I.e. they always have in 2-position a phenyl or a thiophene spacer between the thienithiophene or dithieneothiophene moiety and the triphenylamine or tetraphenylethylene containing moiety R.

Dong Yonggiang et al: "Aggregation-induced emissions of tetraphenylethene derivatives and their utilities as chemical vapor sensors and in organic light-emitting diodes", Applied Physics Letters, vol. 91, no. 1, 5 Jul. 2007 (2007-07-05), pages 011111-1 to 011111-3) discloses tetraphenylethylene derivatives for use as active compounds in OLEDs. The present compounds differ from the structurally closest compounds in this prior art document in the thienothiophene or dithienothiophene ring. Dong Yonggiang et al document does not discloses or suggest any thienothiophene or dithienothiophene derivatives, let alone the 2-phenyl/thiophene substitution pattern of the present compounds.

wherein
$R^2$, $R^3$, $R^4$, $R^5$ and $R^6$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.

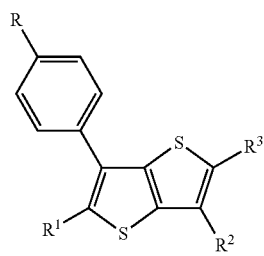

(XI)

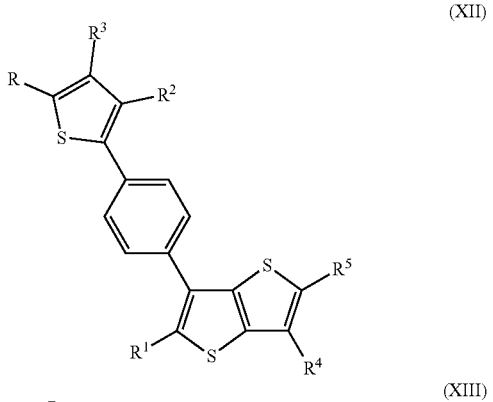

(XII)

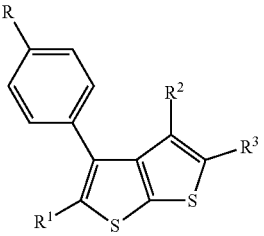

(XIII)

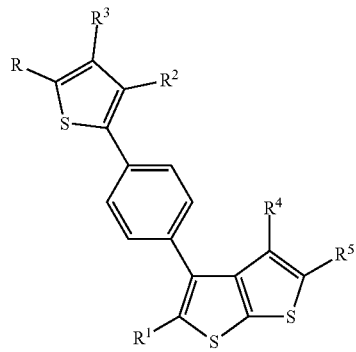

(XIV)

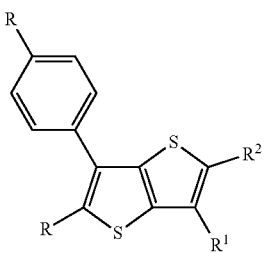

(XV)

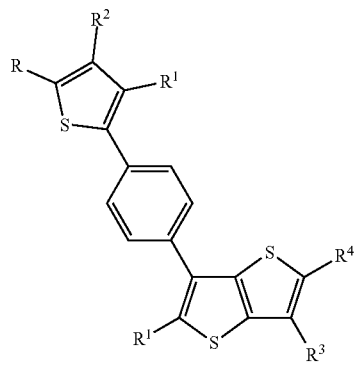

(XVI)

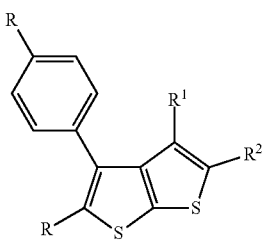

(XVII)

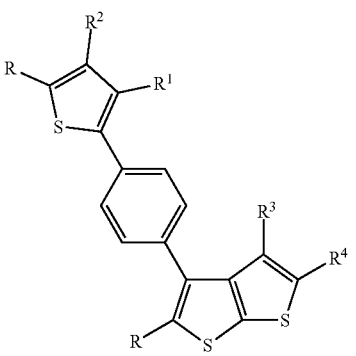

(XVIII)

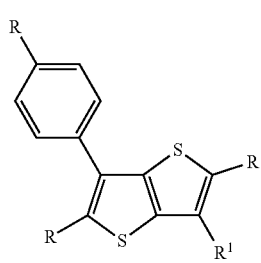
(XIX)
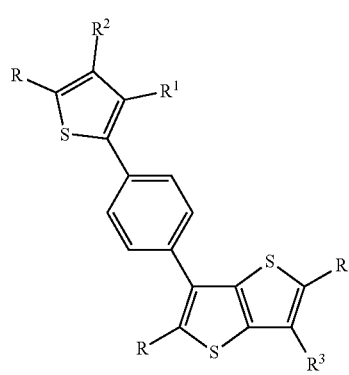
(XX)
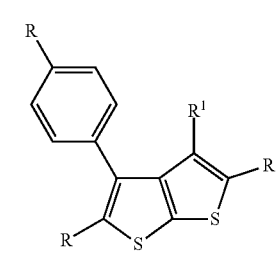
(XXI)
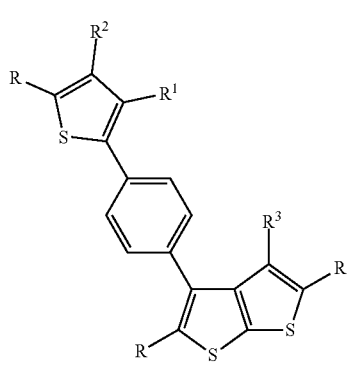
(XXII)
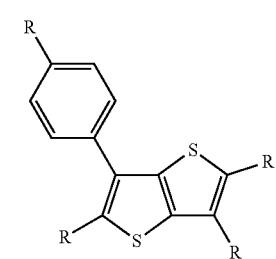
(XXIII)
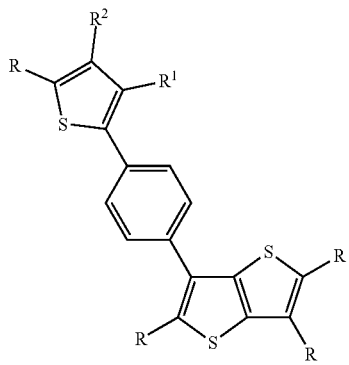
(XXIV)
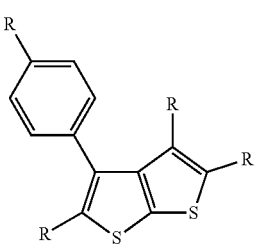
(XXV)
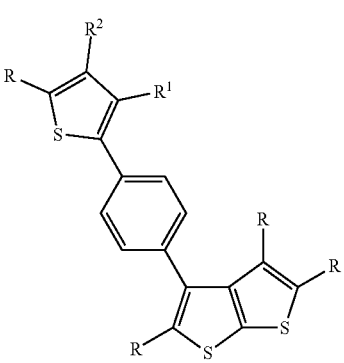
(XXVI)
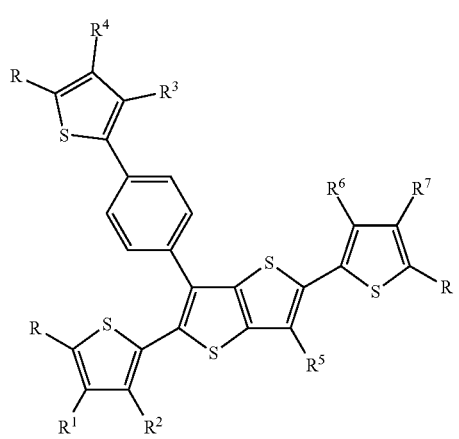
(XXVII)

(XXVIII)
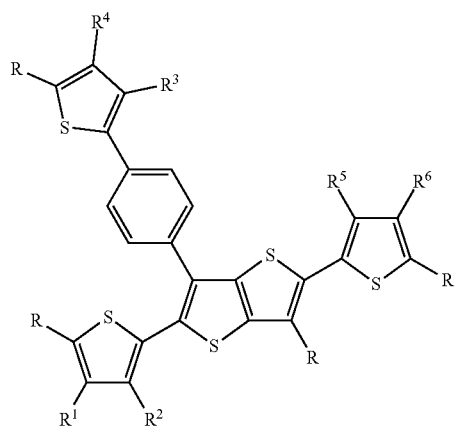
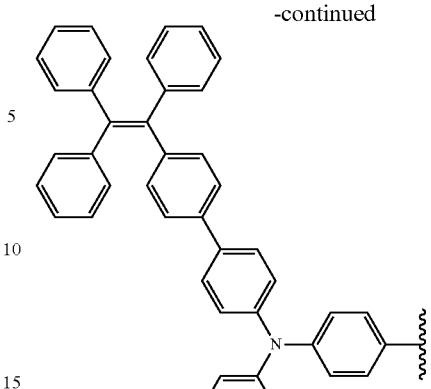
(XXIX)
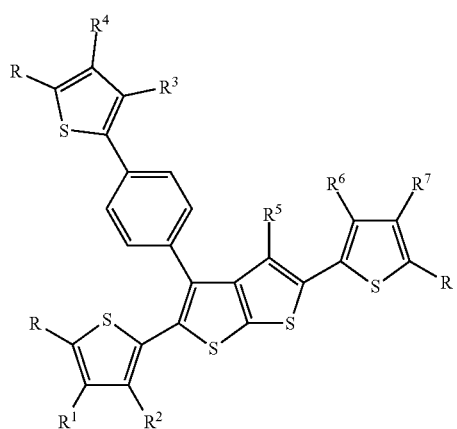
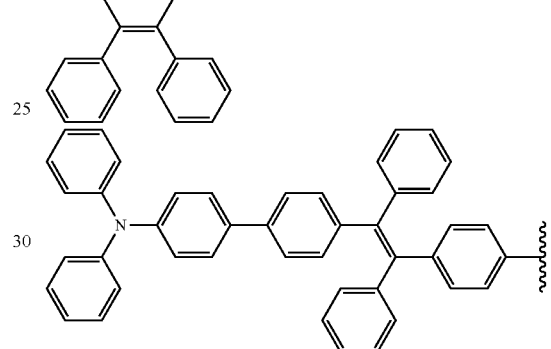
(XXX)
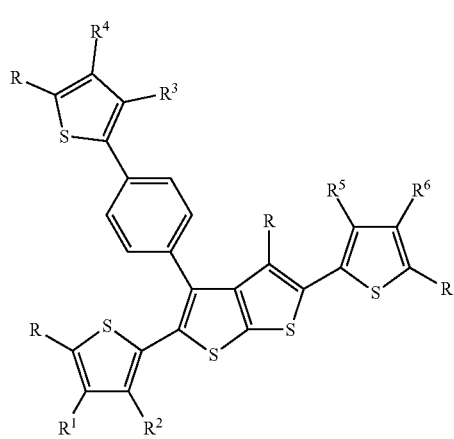
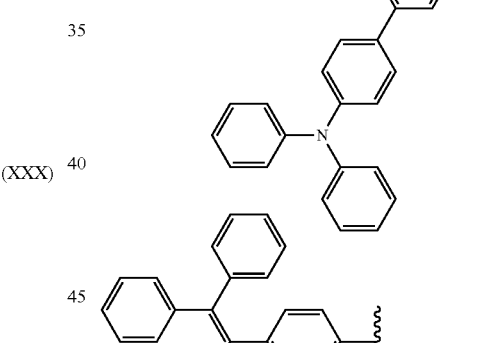
R =
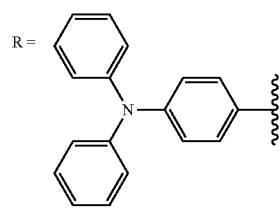
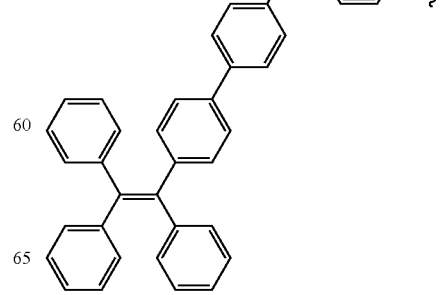

-continued
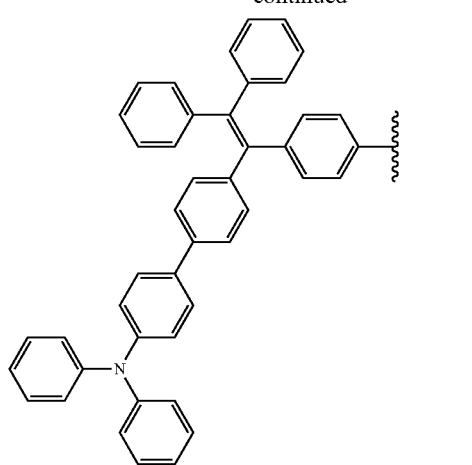
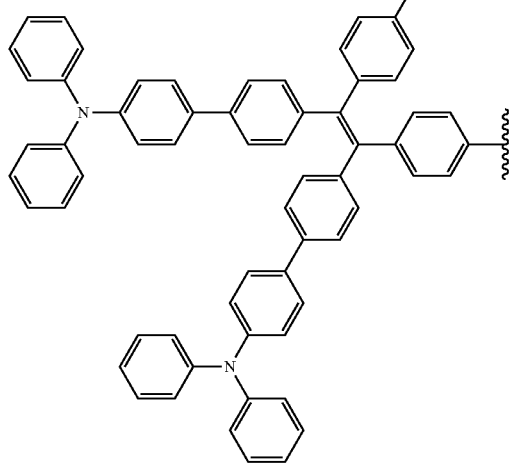
wherein
$R^1$, $R^2$, $R^3$, $R^4$, $R^5$, $R^6$ and $R^7$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.
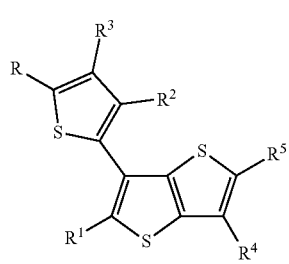
(XXXI)
-continued
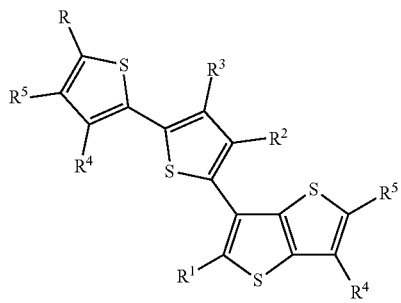
(XXXII)
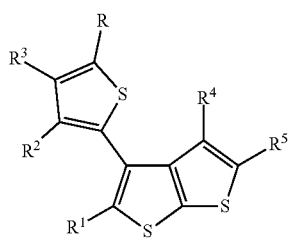
(XXXIII)
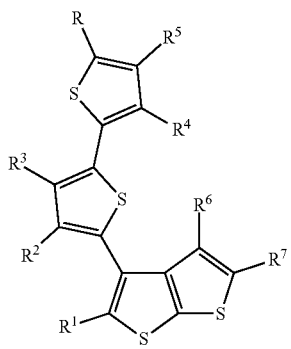
(XXXIV)
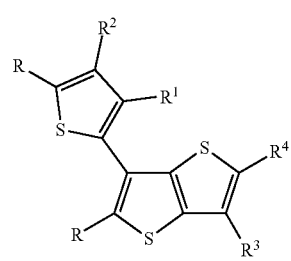
(XXXV)
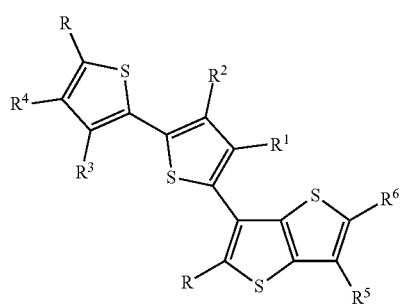
(XXXVI)

(XXXVII)
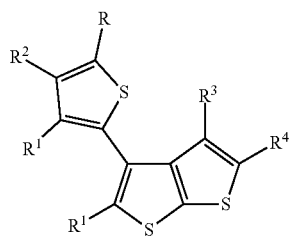
(XXXVIII)
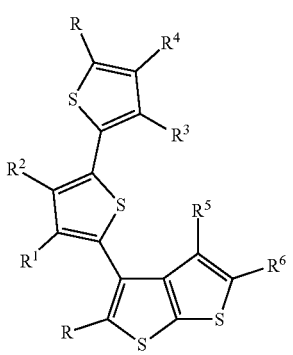
(XXXIX)
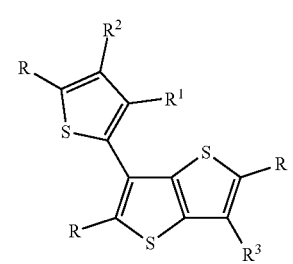
(XL)
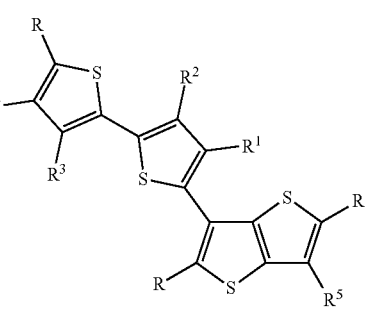
(XLI)
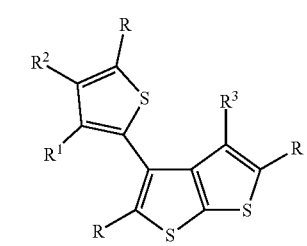
(XLII)
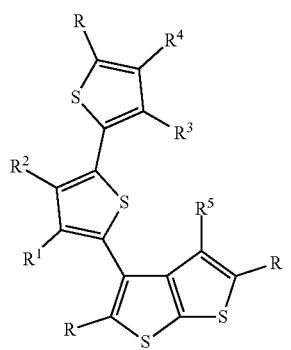
(XLIII)
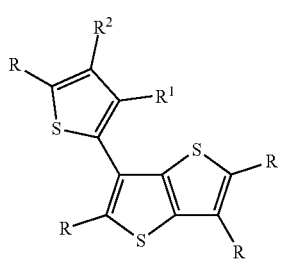
(XLIV)
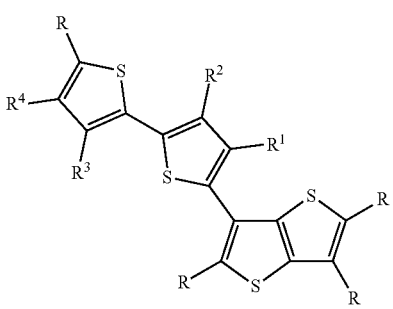
(XLV)
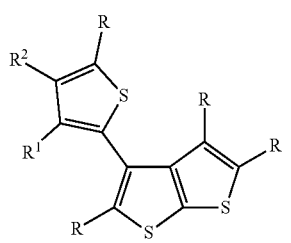
(XLVI)
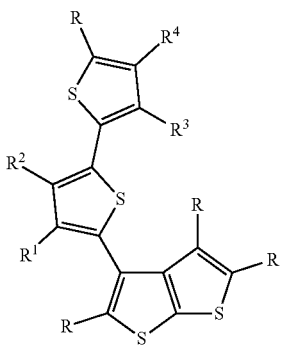

(XLVII)
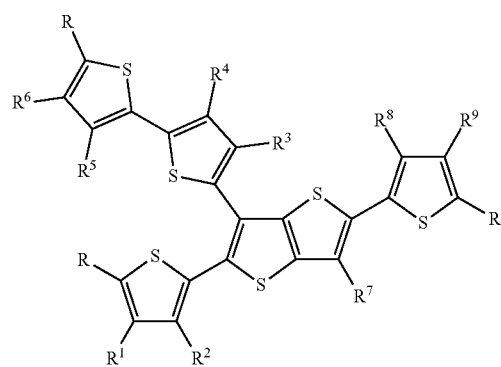
(XLVIII)
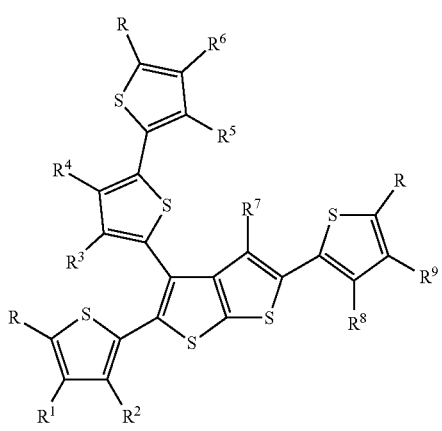
(XLIX)
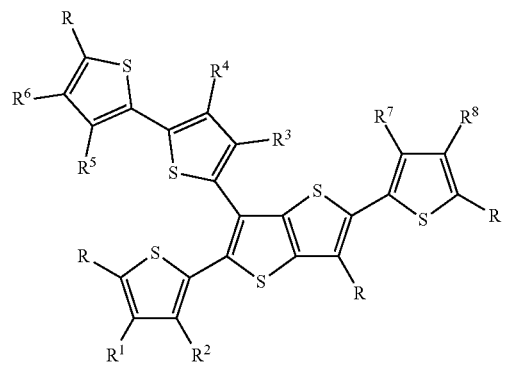
(L)
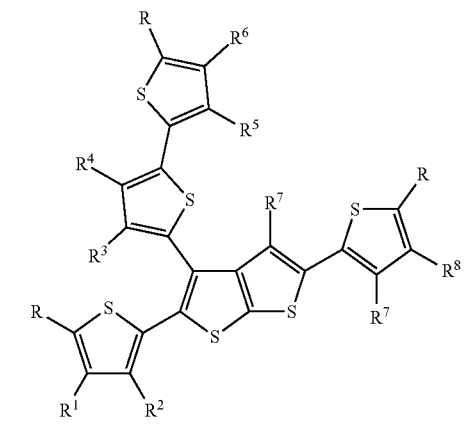
R =
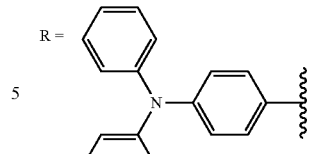
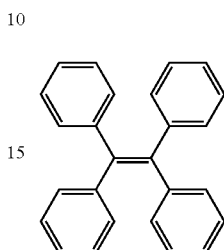
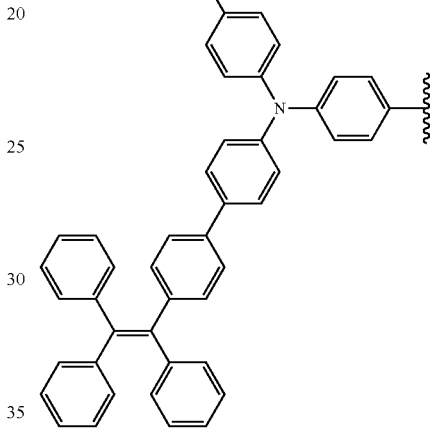
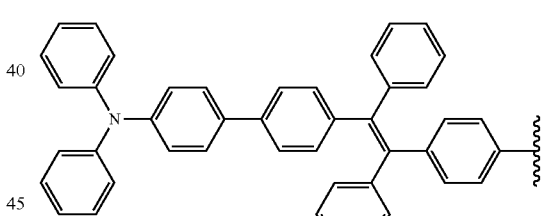
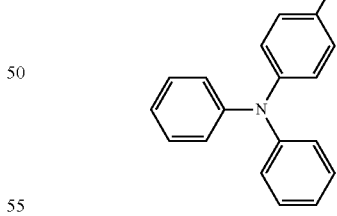
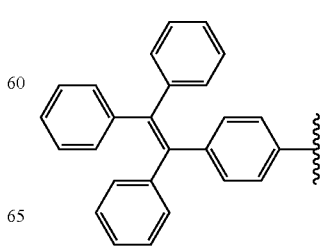

-continued
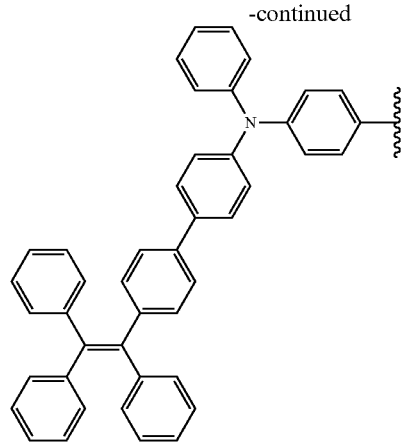
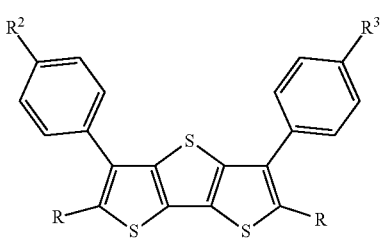
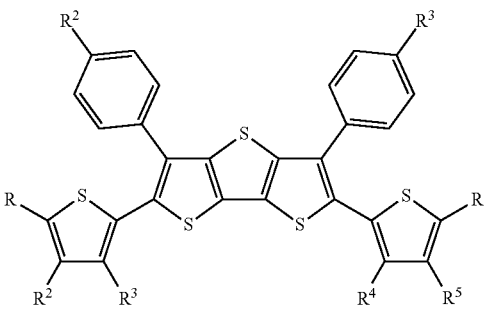
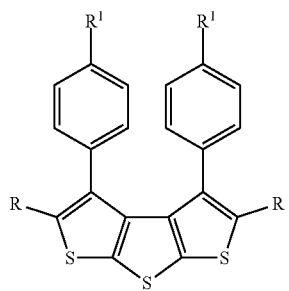
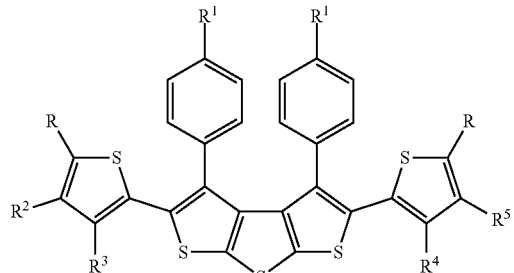
R¹ = —H, —OCH₃, —NO₂, —NH₂, —N(CH₃)₂, —CN
R = 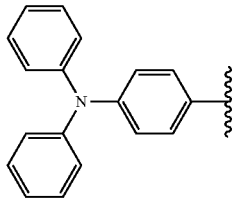
wherein
$R^1$, $R^2$, $R^3$, $R^4$, $R^5$, $R^6$, $R^7$, $R^8$ and $R^9$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate -continued
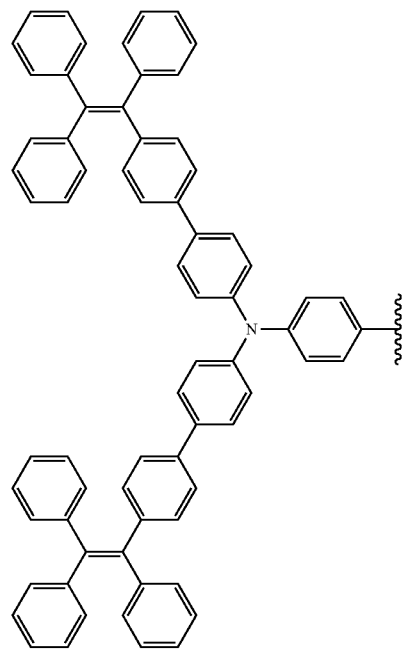
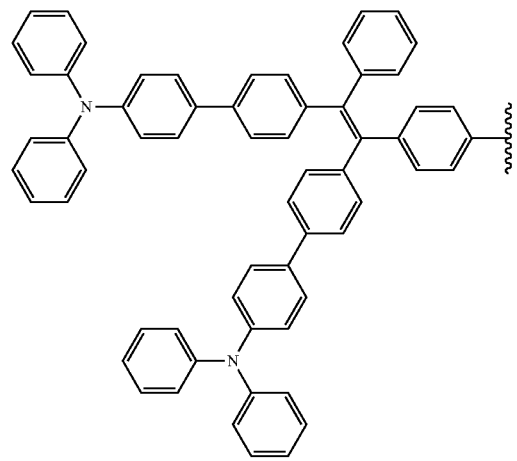
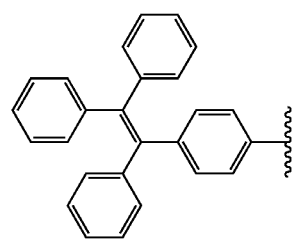
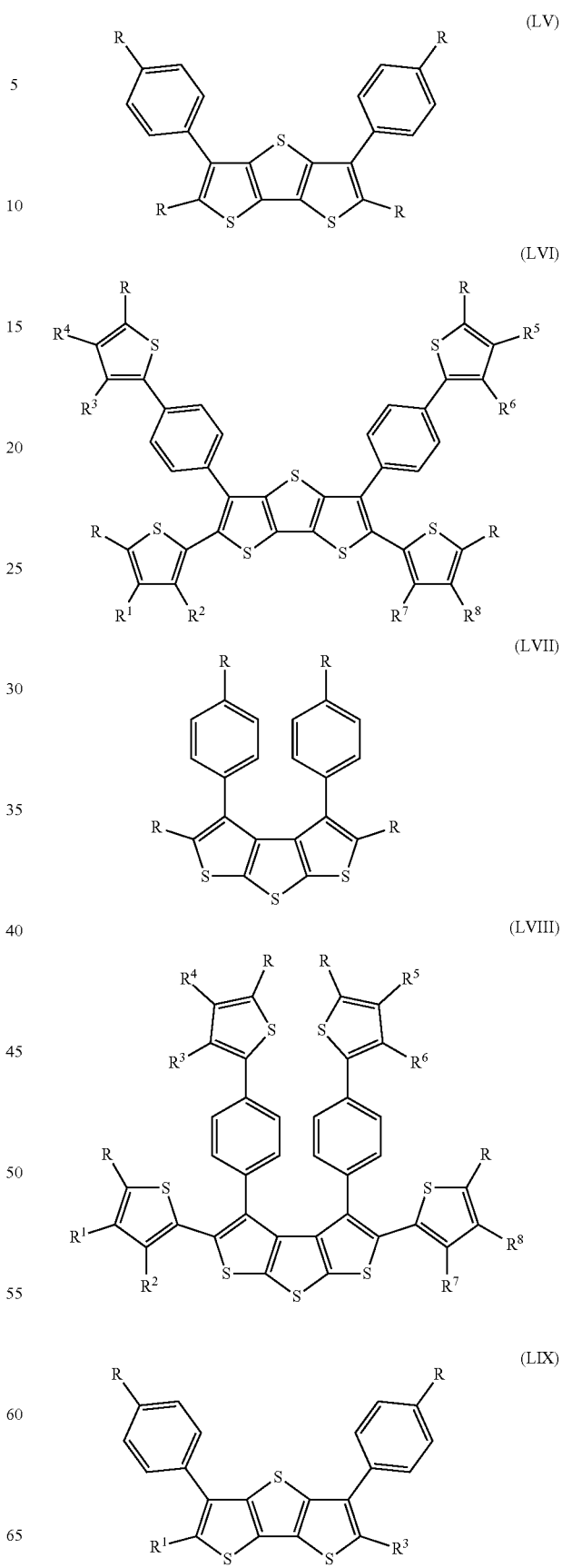
wherein
R², R³, R⁴ and R⁵ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate

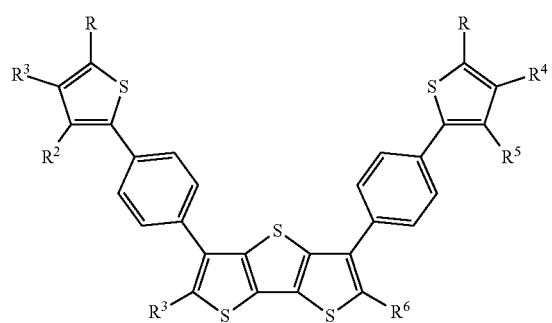
(LX)
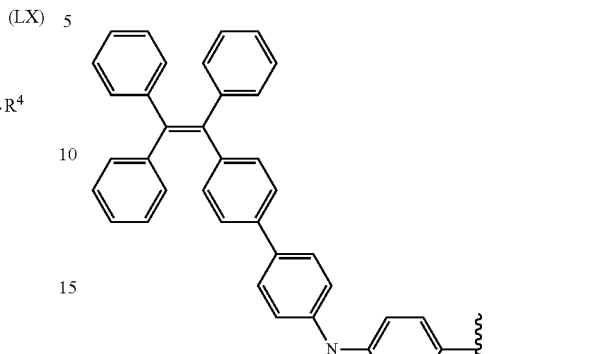
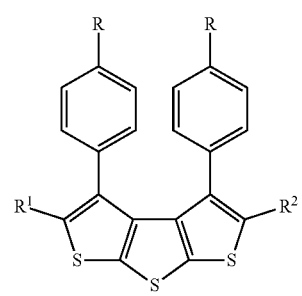
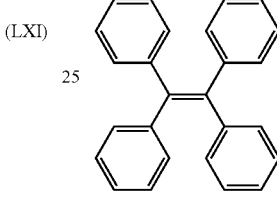
(LXI)
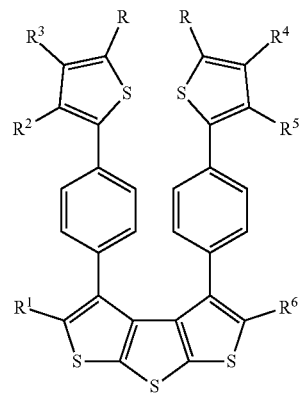
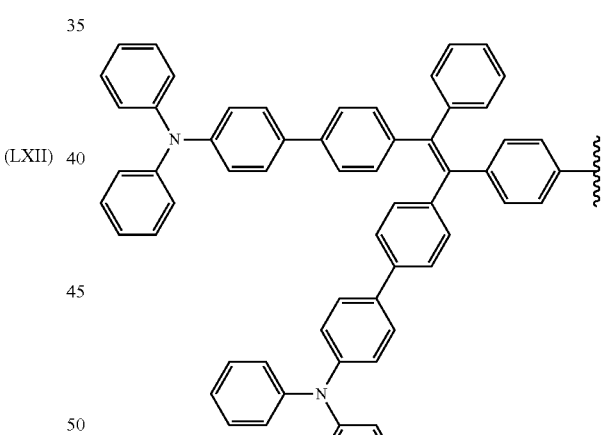
(LXII)
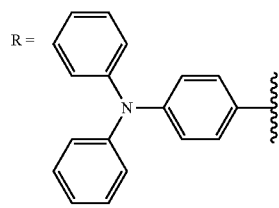
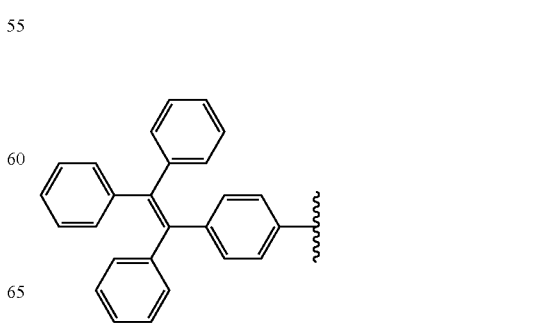

-continued
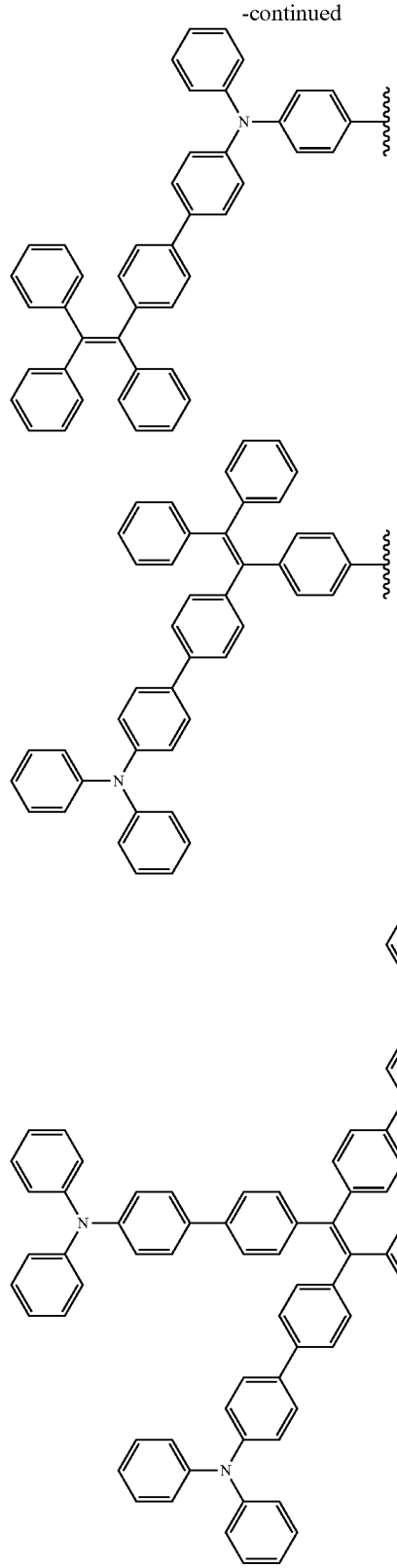
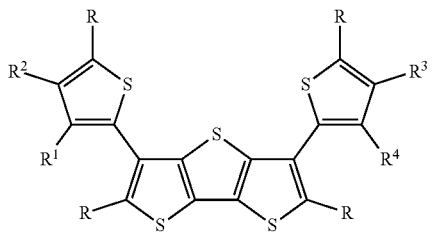
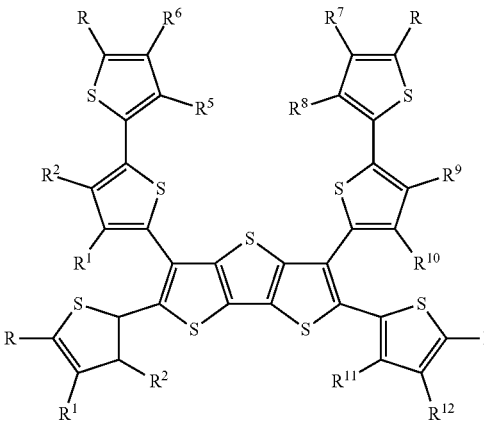
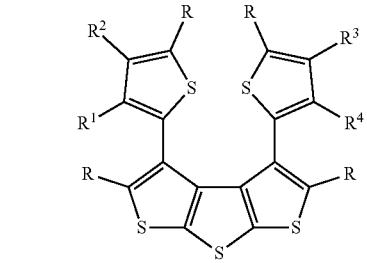
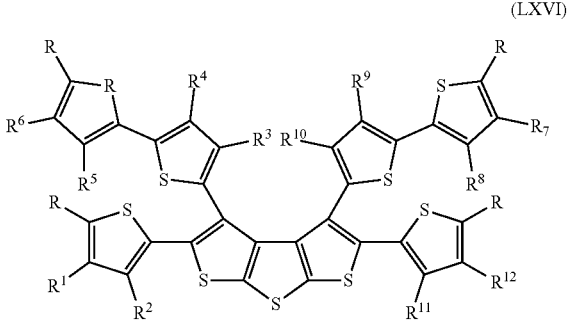
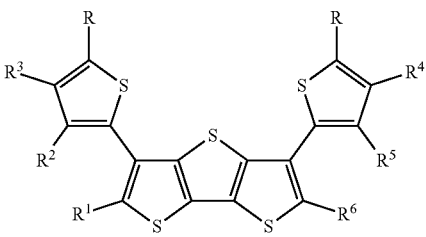
of a group comprising alkyl, aryl, alkenyl, alkynyl, amine, ester, carbonate ester, carbonyl, sulphide, organosilane and thiolate.
wherein
$R^1$, $R^2$, $R^3$, $R^4$, $R^5$, $R^6$, $R^7$ and $R^8$ are independently or equally atom chain(s)/group(s) of about 1 atom to 100 atoms. They may equally or independently have one or more

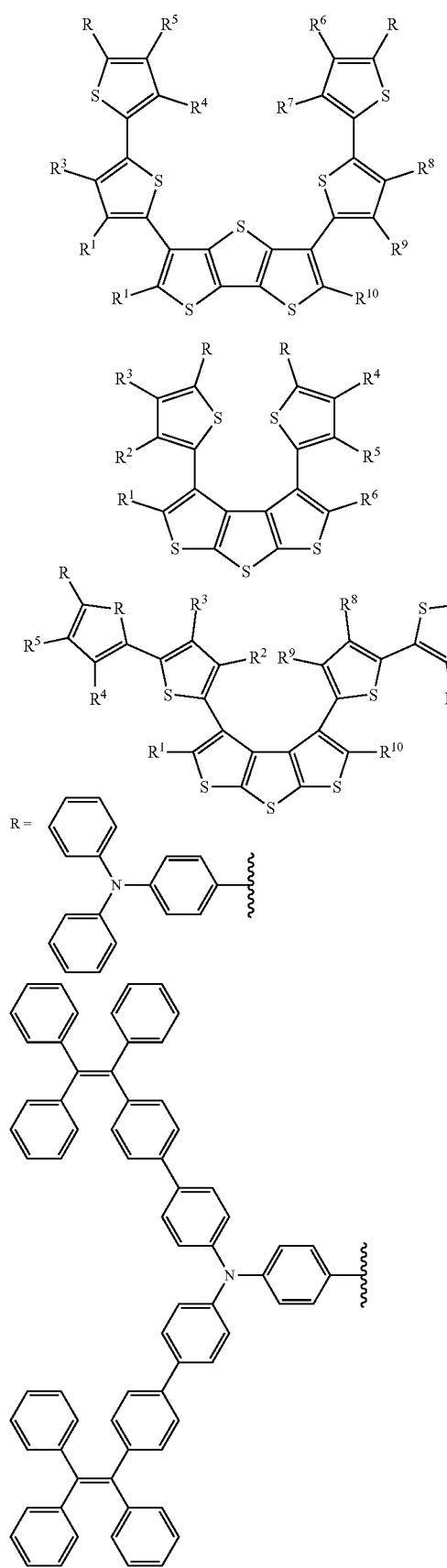

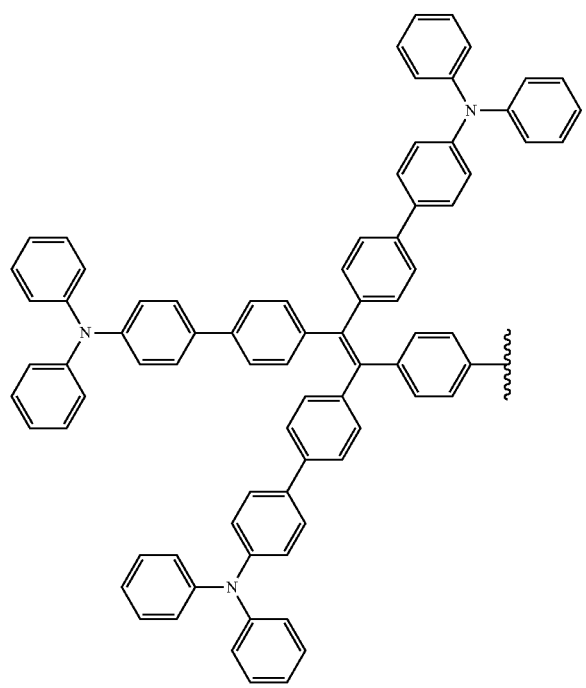

wherein
$R^1$, $R^2$, $R^3$, $R^4$, $R^5$, $R^6$, $R^7$, $R^8$, $R^9$, $R^{10}$, $R^{11}$ and $R^{12}$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.

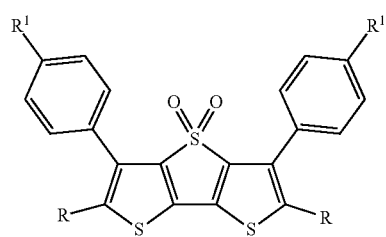

(LXXI)

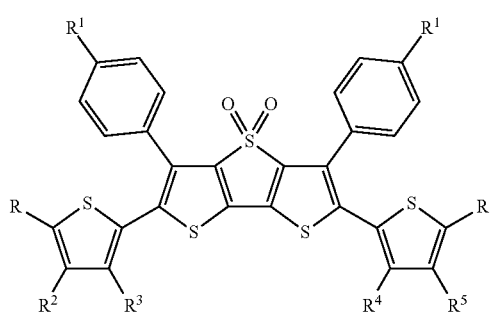

(LXXII)

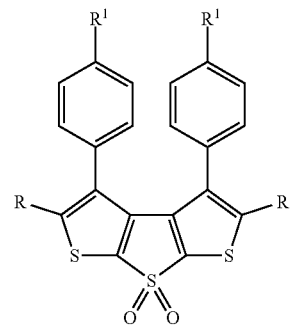

(LXXIII)

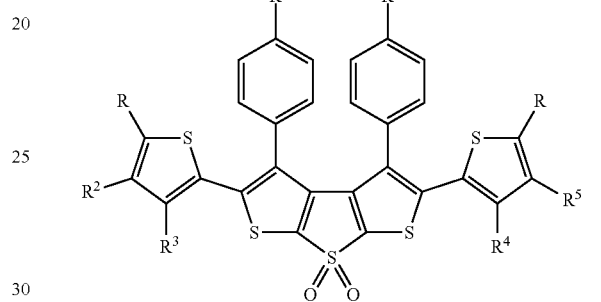

(LXXIV)

$R^1 = $ —H, —OCH$_3$, —NO$_2$, —NH$_2$, —N(CH$_3$)$_2$, —CN

R =

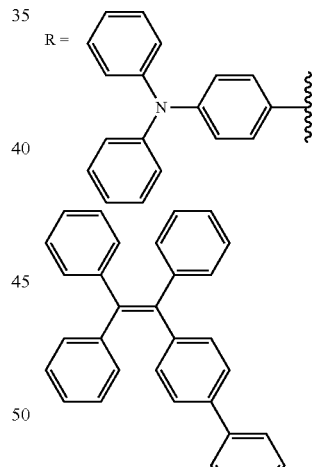

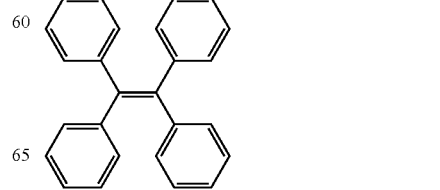

-continued
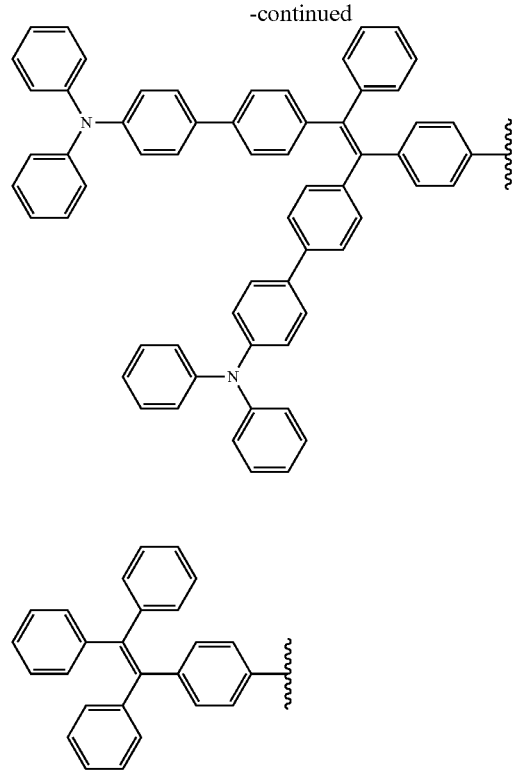
-continued
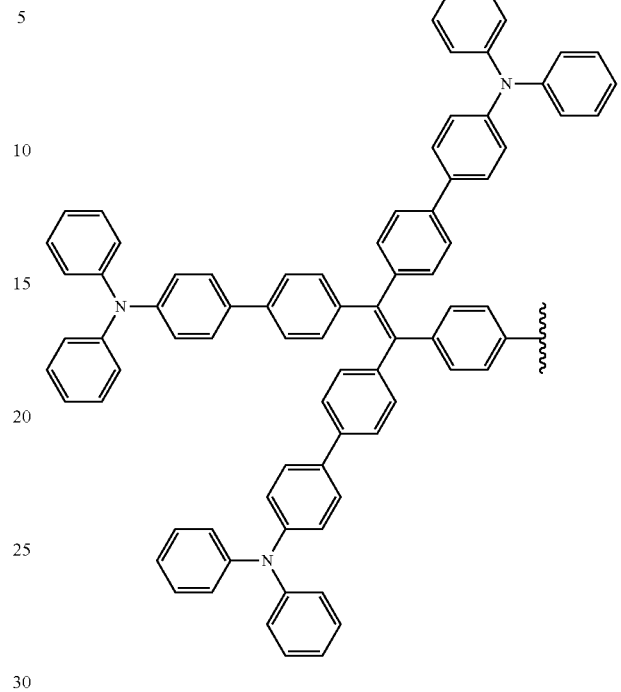
wherein
R², R³, R⁴ and R⁵ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.
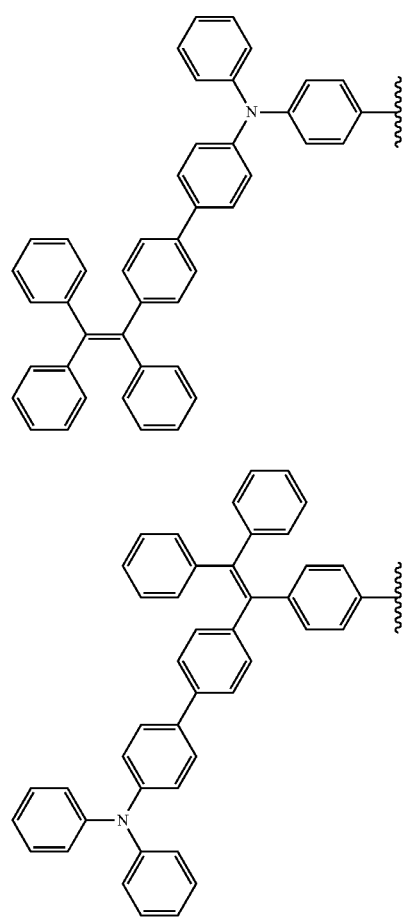
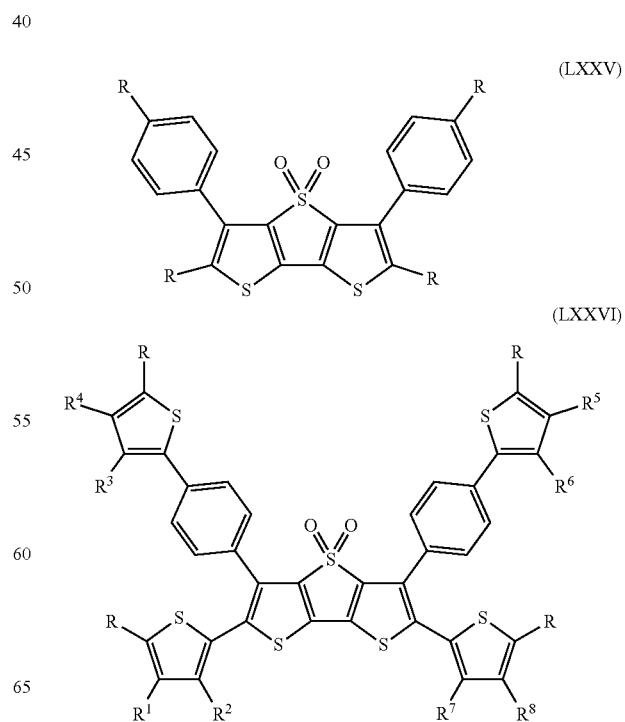

-continued
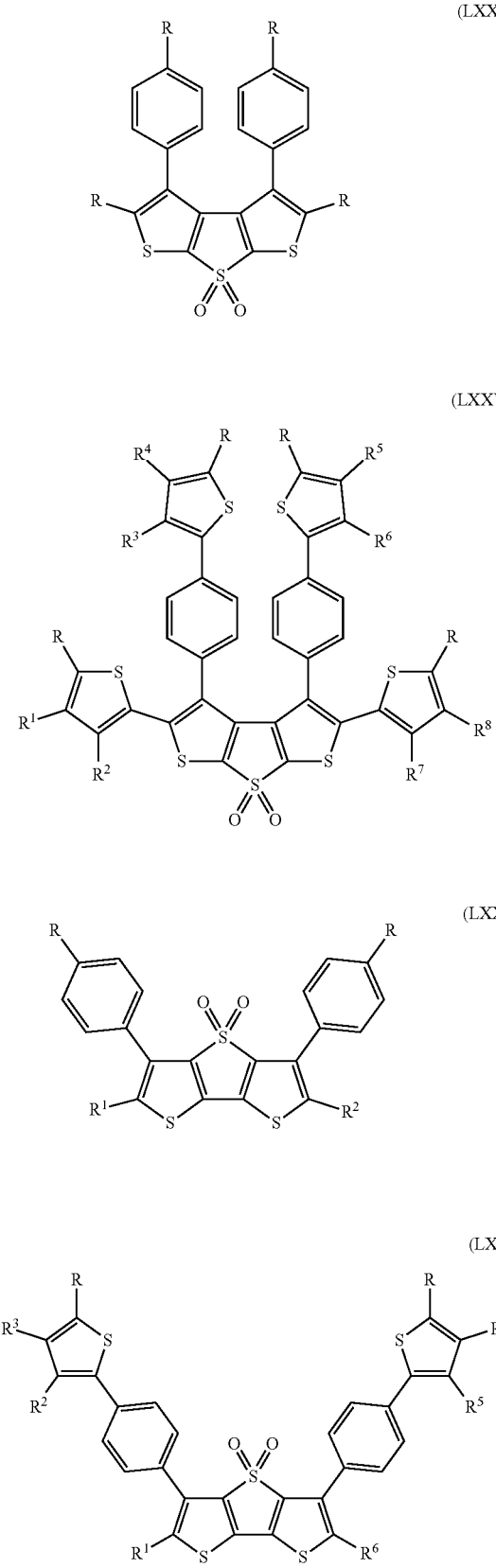
(LXXVII)
(LXXVIII)
(LXXIX)
(LXXX)
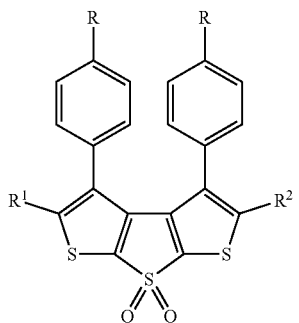
(LXXXI)
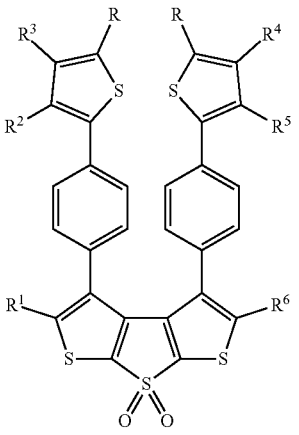
(LXXXII)
R = 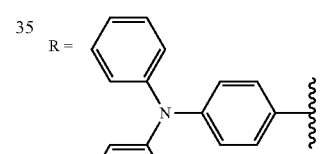
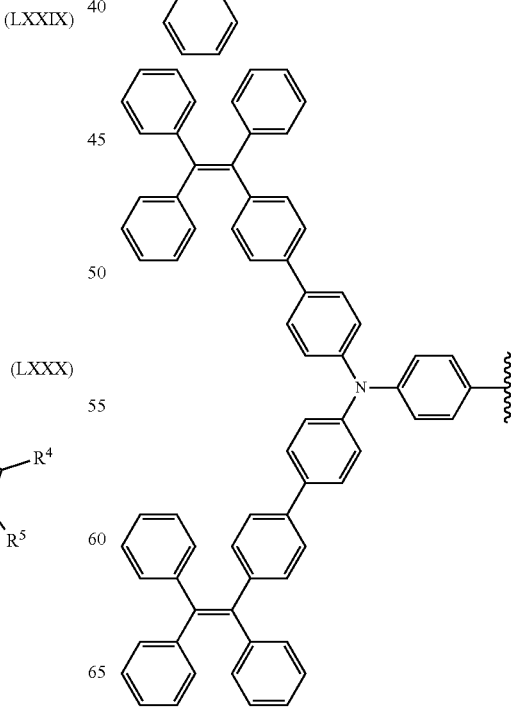

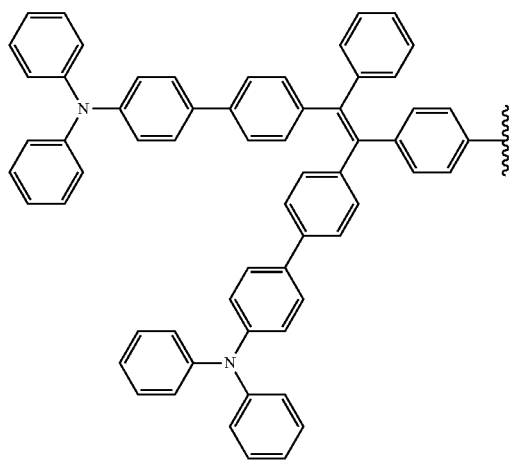
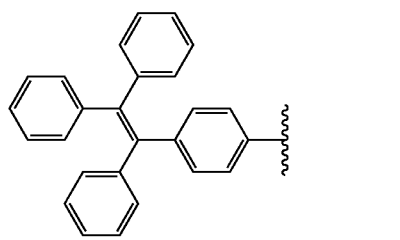
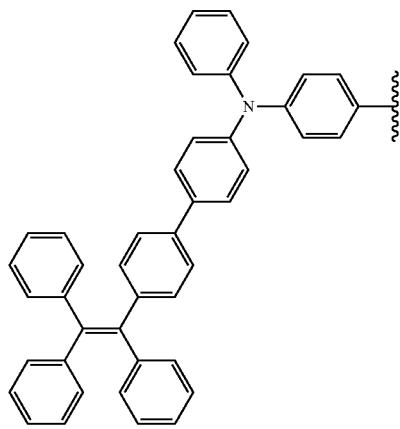
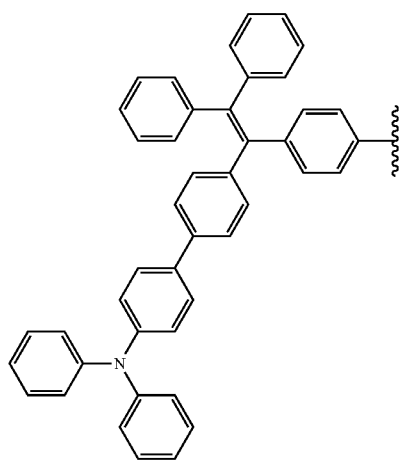
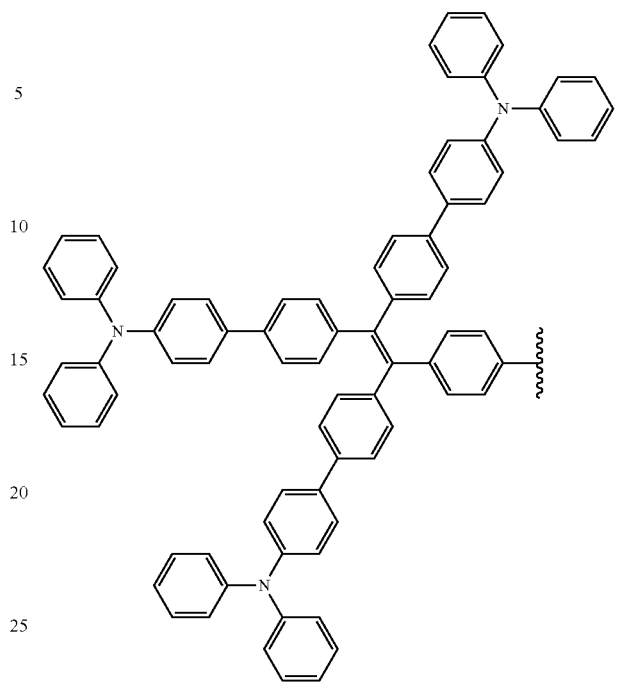
wherein
$R^1$, $R^2$, $R^3$, $R^4$, $R^5$, $R^6$, $R^7$ and $R^8$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.
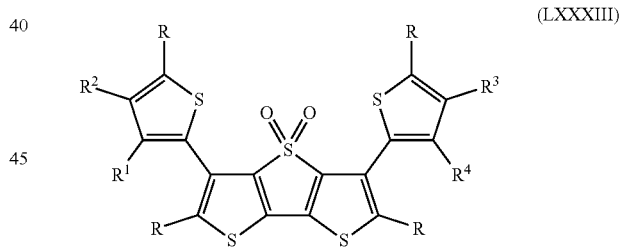
(LXXXIII)
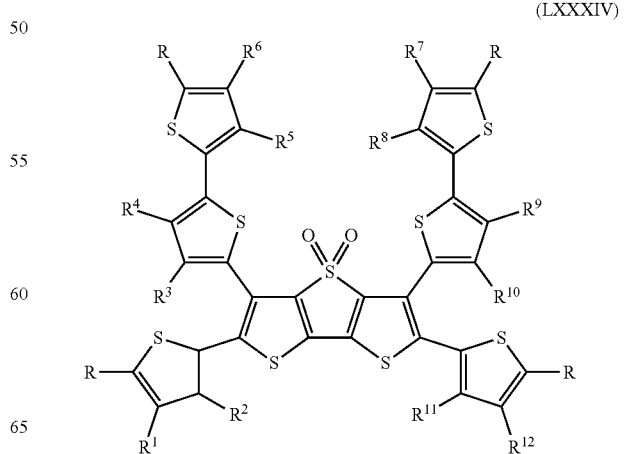
(LXXXIV)

(LXXXV)
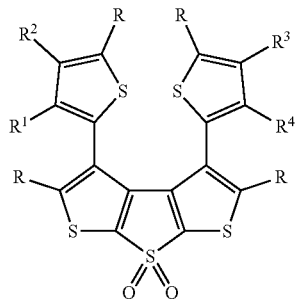
(LXXXVI)
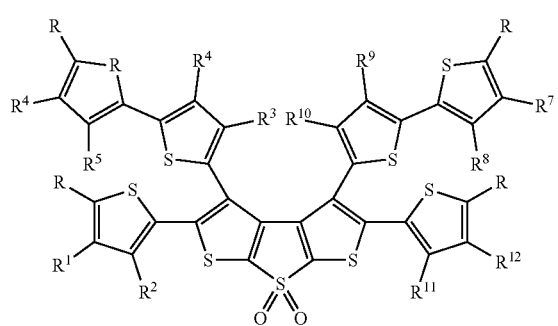
(LXXXVII)
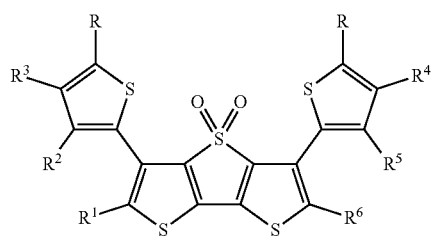
(LXXXVIII)
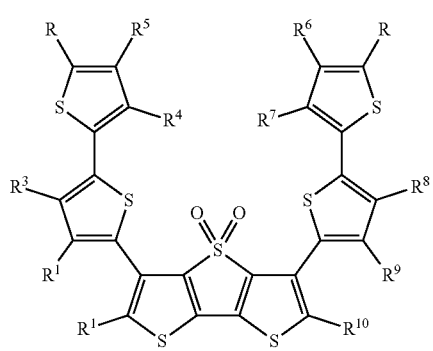
(LXXXIX)
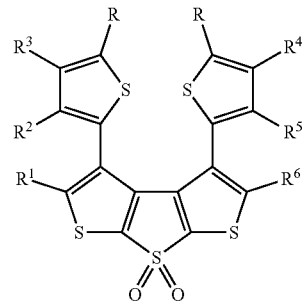
(XC)
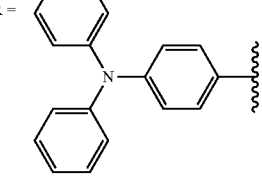
R =
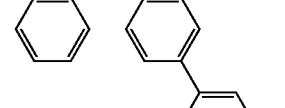
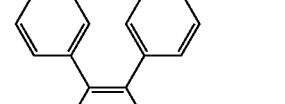

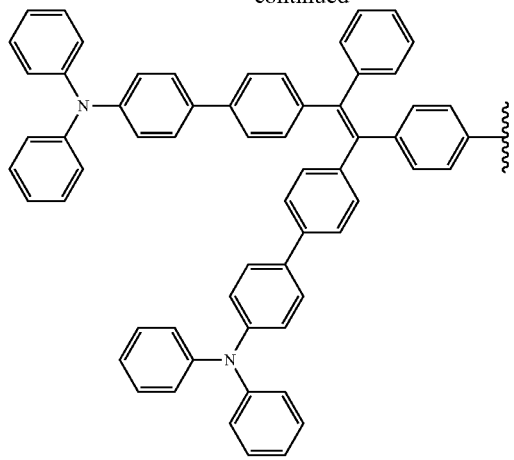

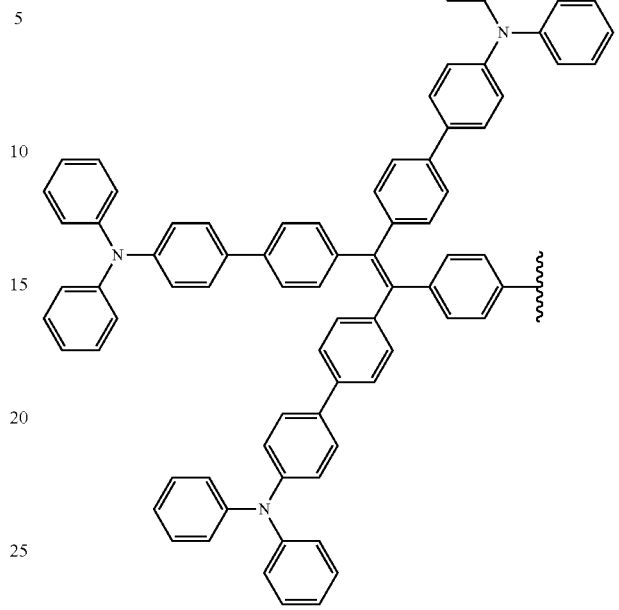

wherein
$R^1$, $R^2$, $R^3$, $R^4$, $R^5$, $R^6$, $R^7$, $R^8$, $R^9$, $R^{10}$, $R^{11}$ and $R^{12}$ are independently or equally atom chain(s)/group(s) of about 1 atom to 100 atoms. They may equally or independently have one or more of a group comprising alkyl, aryl, alkenyl, alkynyl, amine, ester, carbonate ester, carbonyl, sulphide, organosilane and thiolate.

The syntheses of the compounds (I)-(XC) were conducted by Suzuki coupling of the corresponding bromo derivatives of the TT's and DTTs, which had "Br" in place of "R" group(s), with 4,4,5,5-tetramethyl-2-(R)-1,3,2-dioxaborolanes. Bromo-thienothiophenes (TT)s and bromo-dithienothiophenes (DTT)s, having "Br" atom or "Br" atoms in place of "R" groups of (I)-(XC) were synthesized following the literature procedure (T. Ozturk, et. al. *Tetrahedron*, 2005, 61, 11055; E. Ertas, et al. *Tetrahedron, Lett.* 2004, 45, 3405; I. Osken, *Tetrahedron*, 2012, 68, 1216; P. Dundar. *Synth. Met.* 2012, 162, 1010; 1 Osken, *Thin Solid Films*, 2011, 519, 7707; O. Sahin, *Synth. Met.* 2011, 161, 183; O. Mert, *J. Electroanal. Chem.* 2006, 591, 53; A Capan, *Macromolecules* 2012, 45, 8228, I. Osken, *Macromolecules* 2013, 46, 9202) The TTs and DTTs having sulfurs in the rings looking at the same direction were synthesized following the literature method (Gronowitz. S.; Persson, B. Acta Chem. Scand. 1967, 21, 812-813; WO2008/077465).

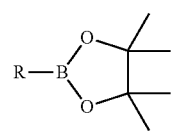

4,4,5,5-Tetramethyl-
2-(R)-1,3,2-
dioxaborolane

EXAMPLE

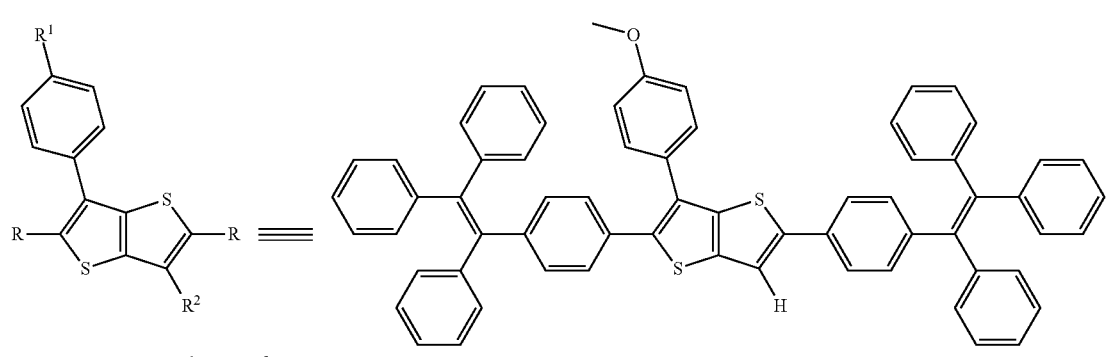

R = Tetraphenylethylene, R¹ = OMe, R² = H

General Method for the Syntheses of (I)-(XC)

Synthesis of 3-(4-methoyphenyl)-2,5-bis(4-(1,2,2-triphenylvinyl)phenyl)thieno[3,2-b]thiophene (III)

In a Schlenk tube, 2,5-dibromo-3-(4-methoxyphenyl)thieno[3,2-b]thiophene (0.5 g, 1.24 mmol), 4,4,5,5-tetramethyl-2-(4-(1,2,2triphenylvinyl)phenyl)-1,3,2-dioxaborolane (1.421 g, 3.1 mmol) and $K_2CO_3$ (0.856 g, 6.2 mmol) was degassed under high vacuum. Degassed THF (18 mL) and water (2 mL) were added to the mixture and the solution was degassed with nitrogen. Tetrakis(triphenylphosphine)palladium(0) (72 mg, 0.062 mmol) was then added under nitrogen atmosphere. The mixture was stirred at 75° C. for 2 days and allowed to cooled to room temperature. To the reaction mixture was added to water (150 mL) and extracted with dichloromethane (DCM) (3×50 mL). The collected organic layers was washed with water and brine twice, and then dried over $NaSO_4$. After removal of the solvent under reduced pressure, the crude product was purified by column chromatography over silica gel using a mixture of n-hexane/dichloromethane (5:1) as eluent. The product was obtained as a yellow solid in 78% yield, $^1H$ NMR (500 MHz, $CDCl_3$) δ 7.42 (s, 1H), 7.37 (d, J=8.28 Hz, 2H), 7.34 (d, J=8.75 Hz, 2H), 7.11 (m, 34H), 6.94 (d, J=8.32 Hz, 2H), 6.89 (d, J=8.77 Hz. 2H), 3.87 (s, 3H) ppm; $^{13}C$ NMR (125 MHz, $CDCl_3$): δ 144.83, 143.68, 143.62, 143.58, 143.53, 143.36, 143.29, 143.06, 141.36, 140.92, 140.49, 140.30, 138.80, 137.02, 132.76, 132.63, 131.95, 131.45, 131.43, 131.40, 131.38, 131.34, 131.08, 128.42, 127.85, 127.76, 127.71, 127.69, 127.66, 127.60, 126.64, 126.57, 126.55, 126.50, 124.80, 115.44, 114.14, 55.24 ppm.

Example of a Device Fabrication:

Organic light emitting devices were fabricated by depositing the small molecules by thermal evaporation onto electrically conductive substrates. Indium tin oxide (ITO), coated (15 ohms/sq) on a glass substrate, was employed as an anode electrode. N,N'-Di(1-naphthyl)-N,N'-diphenyl-(1,1'-biphenyl)-4,4'-diamine [NPB] (60 nm) as a hole injection layer was deposited on ITO. Subsequently, the small molecule film (20 nm), as an active layer, 1,3,5-tris(N-phenylbenzimiazole-2-yl)benzene [TPBI] (10 nm) as an electron injection layer and tris(8-hydroxyquinolinato)aluminium [Alq3] (20 nm) were coated as an electron transfer layer by thermal evaporation technique under high vacuum (~$10^{-6}$ mbar). Finally, LiF (1 nm) and aluminum (Al, 120 am) were deposited under vacuum (~$10^{-6}$ mbar) by thermal evaporation technique to assemble the cathode electrode.

Figure 1:
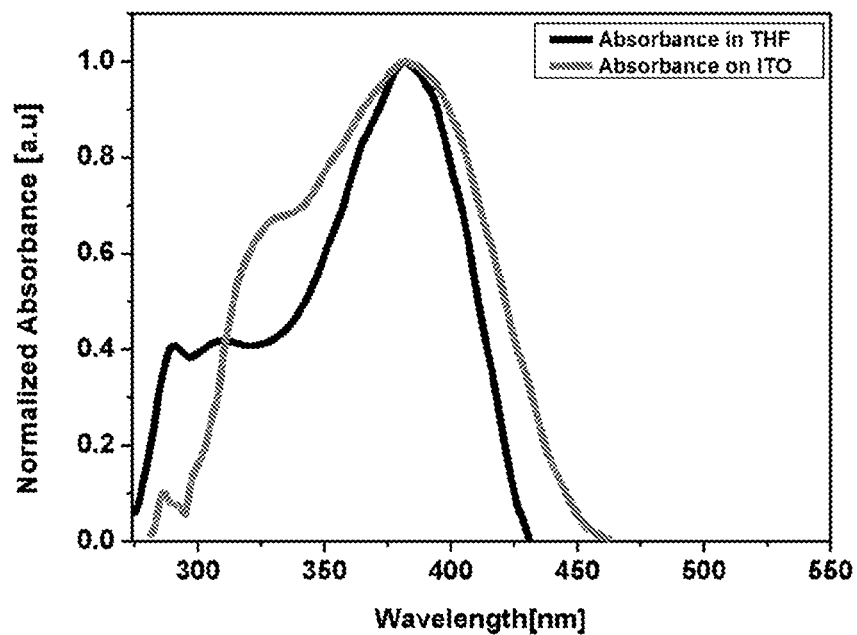
FIG. 1. UV-Vis spectra of the molecule (III) (where R=tetraphenylethylene, $R^1$=OMe and $R^2$=H) in tetrahydrofuran (THF) and in the solid state (on ITO coated glass) at room temperature.
Figure 2:
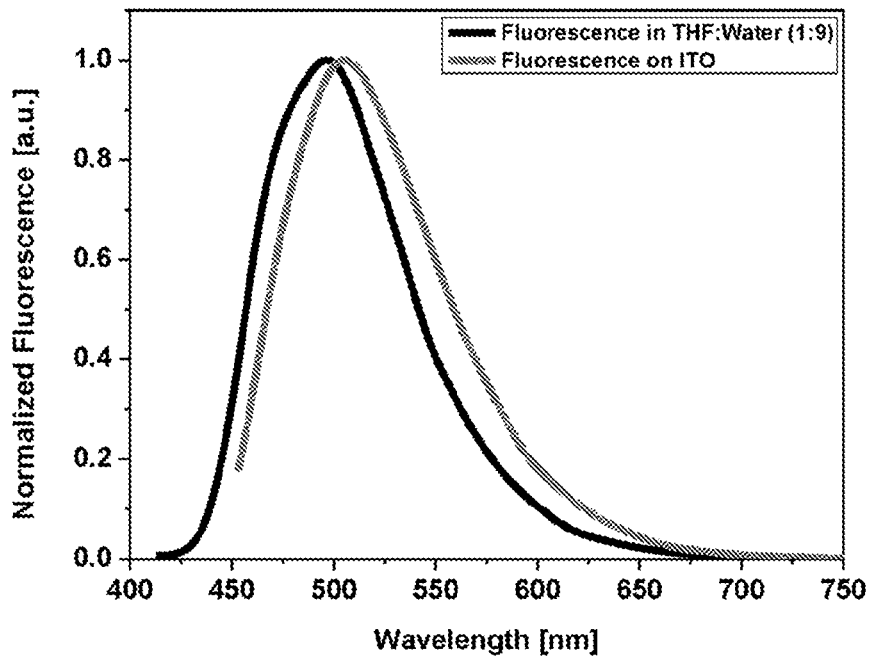
FIG. 2. Fluorescence spectra of the molecule (III) (where R=tetraphenylethylene, $R^1$=OMe and $R^2$=H) in tetrahydrofuran (THF) and in the tetrahydrofuran/water (1/9) mixture at room temperature.
Figure 3:
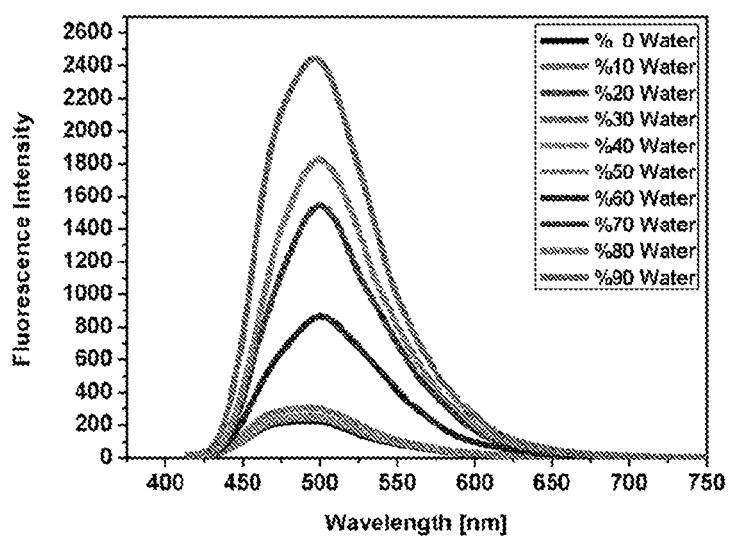
FIG. 3. Fluorescence spectra of the molecule (Ill) (where R=tetraphenylethylene, $R^1$=OMe and $R^2$=H) in the THF-water mixtures with different water contents at room temperature.
Figure 4:
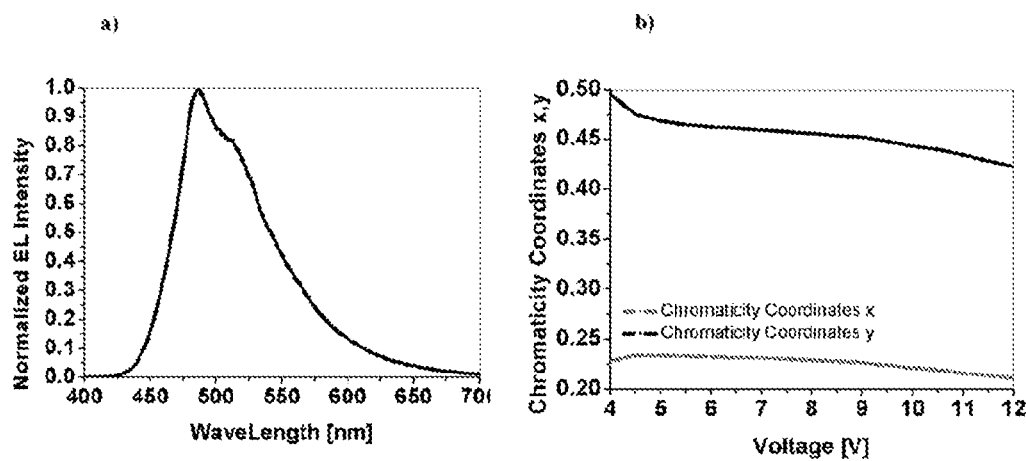
FIG. 4. a) Electroluminescent spectrum of the fabricated device of the molecule (III) (where R=tetraphenylethylene, $R^1$=OMe and $R^2$=H): b) CIE coordinates of the fabricated device of the molecule (III) at different voltages. The electroluminescent spectrum covers the region almost from 450 nm to 650 nm. Color coordinates are in the region for bluish green color according to the CIE 1931 Chromaticity Diagram.
Figure 5:
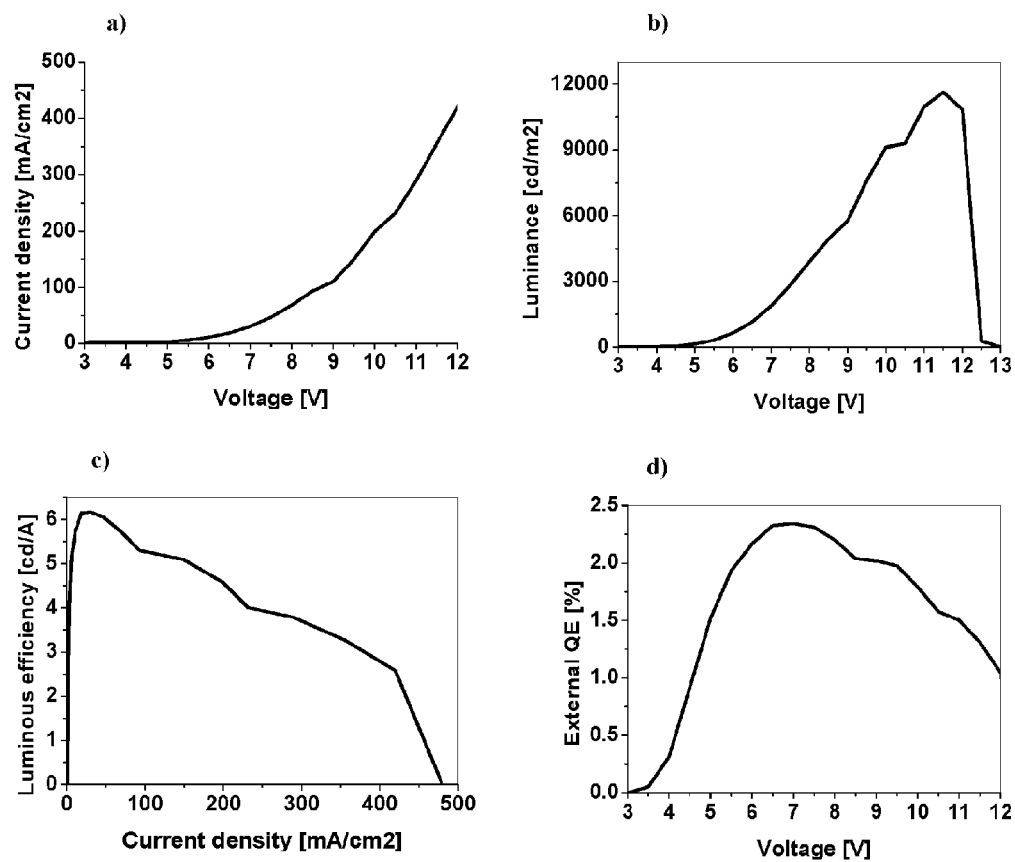
FIG. 5. OLED device characteristics: a) voltage-current b) luminance-voltage c) luminous efficiency-current density and d) external quantum efficiency-current density.

We claim:

1. A polymer or small molecule comprising one or more formulas selected from a group consisting of formulas (I), (II), (III), (IV), (V), (VI), (VII), (VIII), (XIX) and (X), as follows,

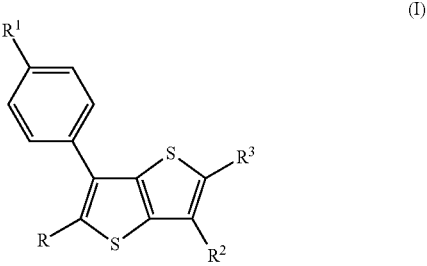

(II)
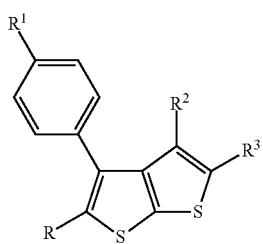
(III)
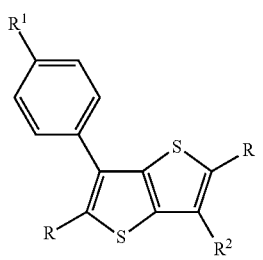
(IV)
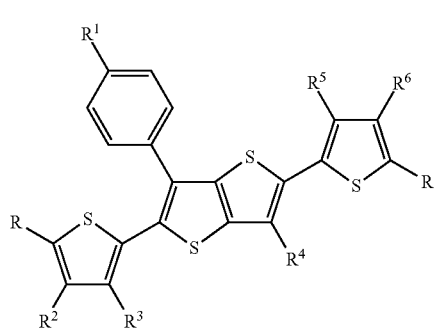
(V)
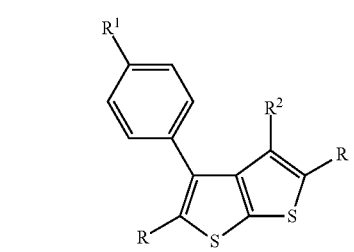
(VI)
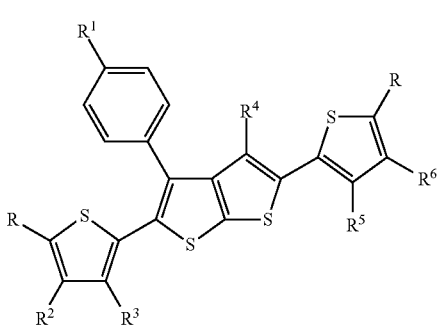
(VII)
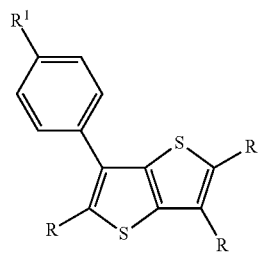
(VIII)
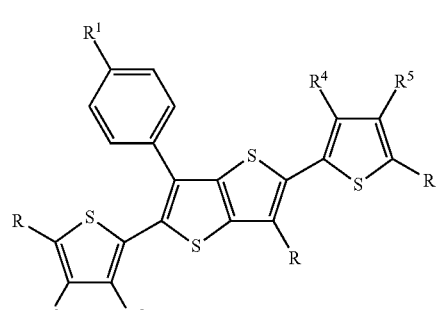
(IX)
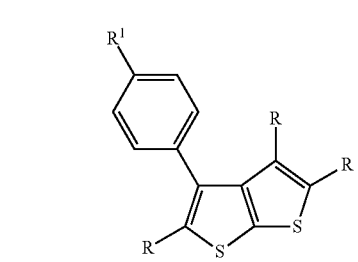
(X)
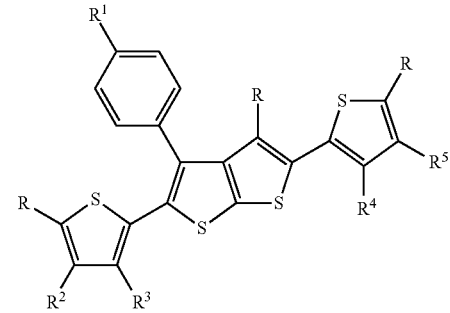
wherein $R^1$ is selected from a group consisting of —H, —OCH$_3$, —NO$_2$, —NH$_2$, —N(CH$_3$)$_2$, —CN; and wherein R is selected from a group consisting of:
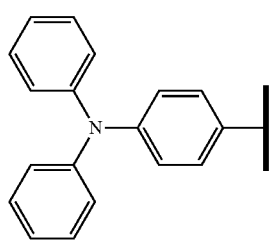

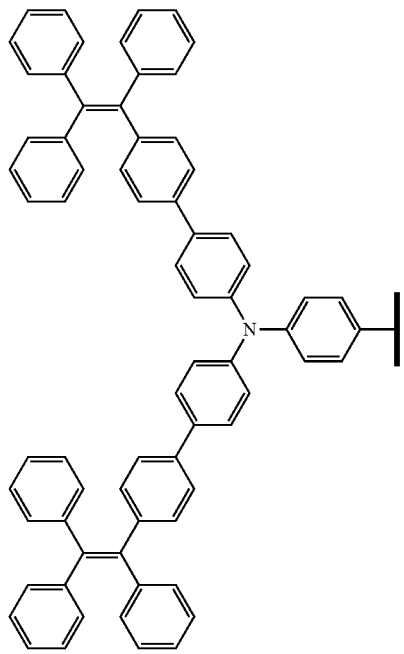
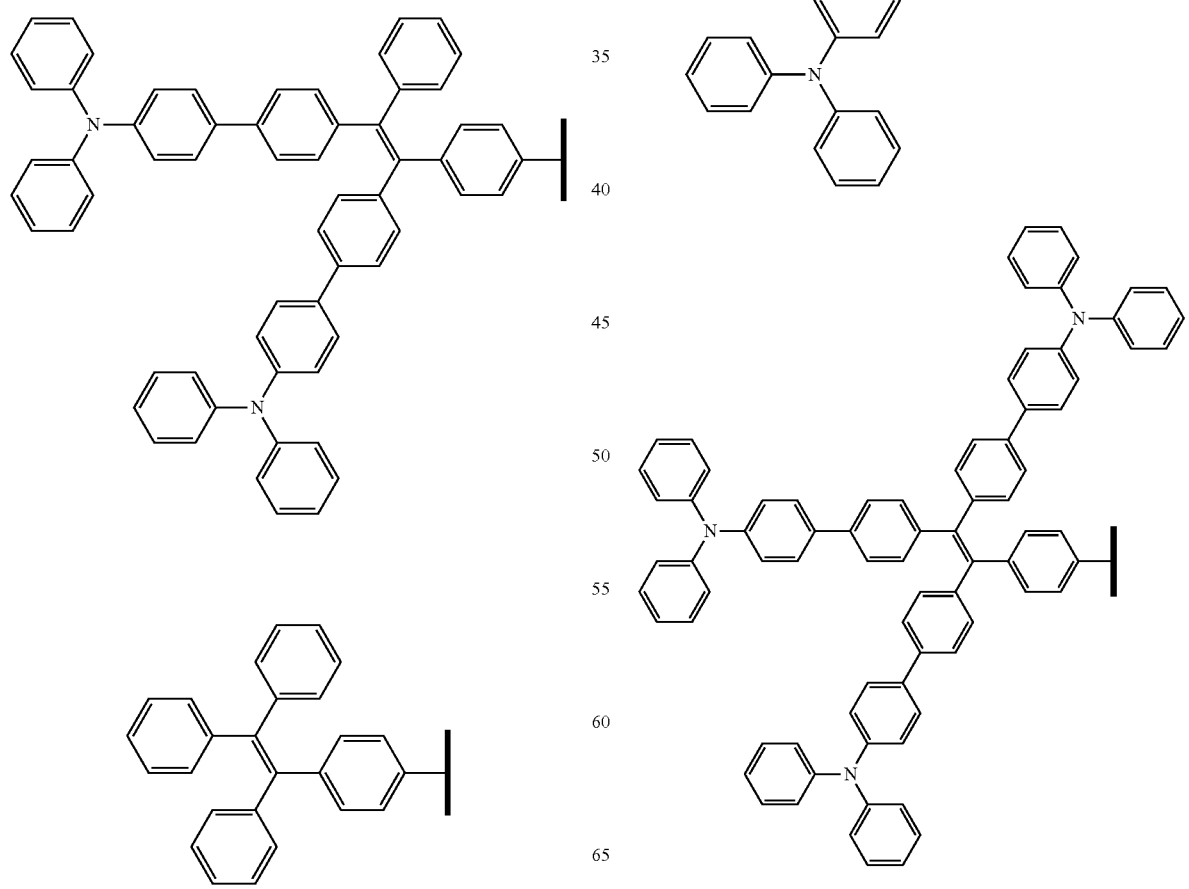

and

R², R³, R⁴, R⁵ and R⁶ are atom chain(s)/group(s) of 1 atom to 100 atoms and wherein one or more of R², R³, R⁴, R⁵ and R⁶ comprise at least one of an alkyl, aryl, alkenyl, alkynyl, amine, ester, carbonate ester, carbonyl, sulphide, organosilane or thiolate group.

2. A blend comprising one or more compounds given in disclosed in claim 1.

3. A formulation comprising one or more compounds disclosed in claim 1.

4. A blend or formulation comprising one or more compounds disclosed in claim 1, wherein the blend or formulation is used in at least one of charge transport, electrically conducting, semiconducting, photoconducting or light emitting materials in electronic, optical, electrooptical, electroluminescent or photoluminescent or devices.

5. A polymer or small molecule comprising one or more formulas selected from a group consisting of formulas (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX) and (XXX) as follows:

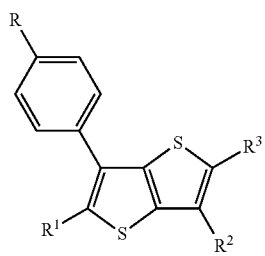
(XI)

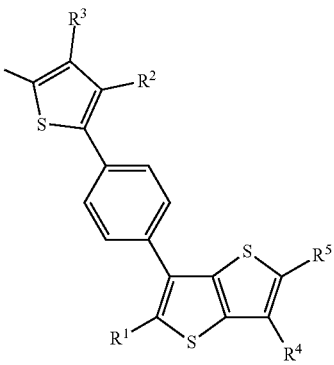
(XII)

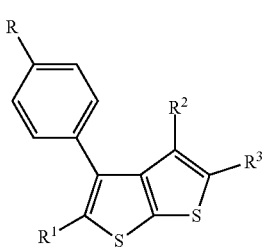
(XIII)

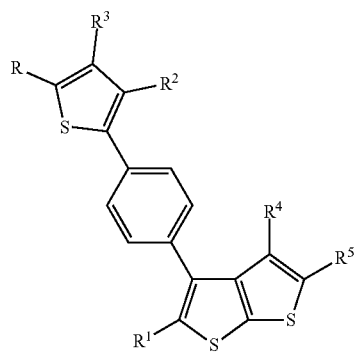
(XIV)

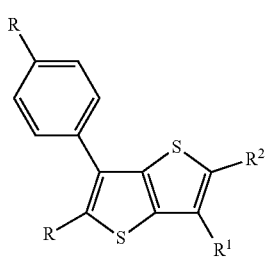
(XV)

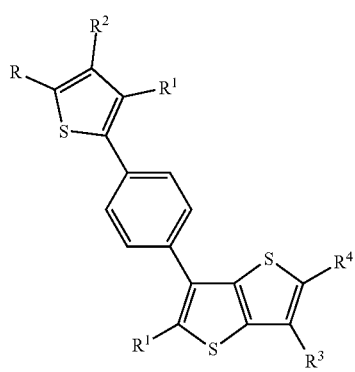
(XVI)

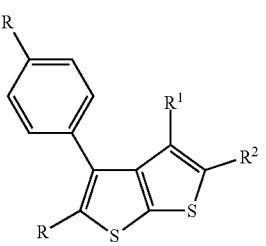
(XVII)

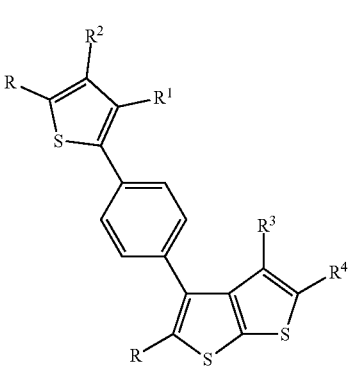
(XVIII)

(XIX)
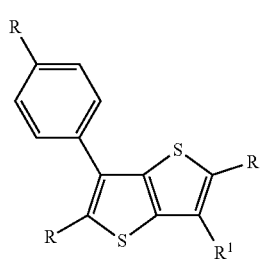
(XX)
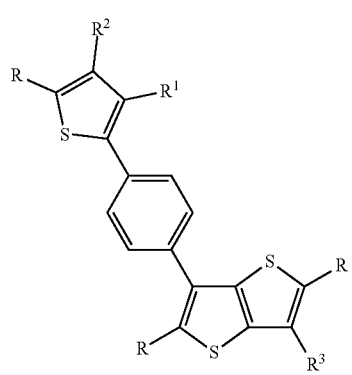
(XXI)
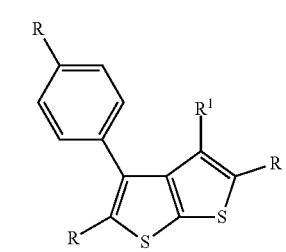
(XXII)
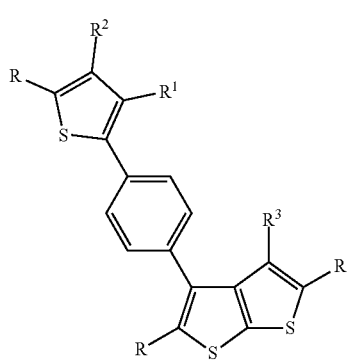
(XXIII)
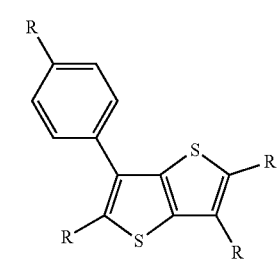
(XXIV)
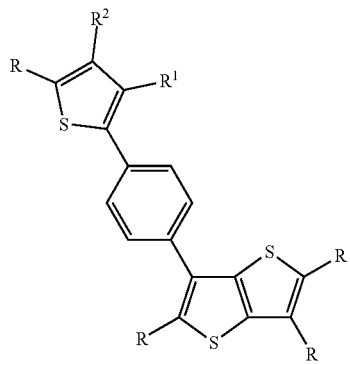
(XXV)
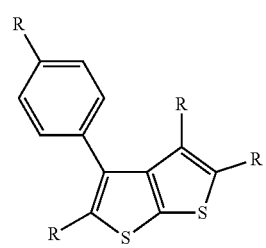
(XXVI)
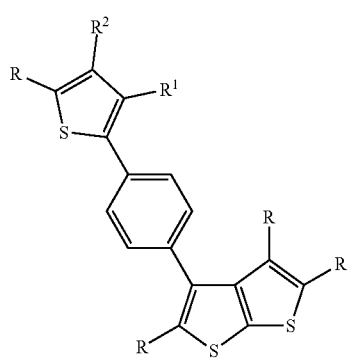
(XXVII)
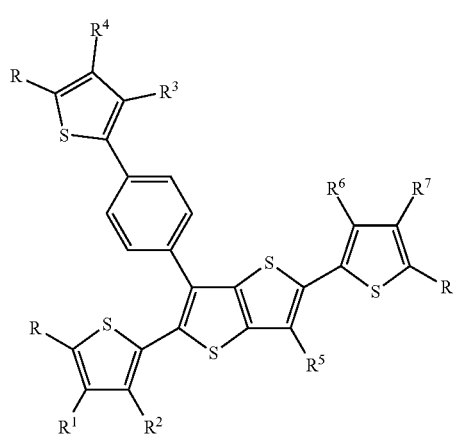

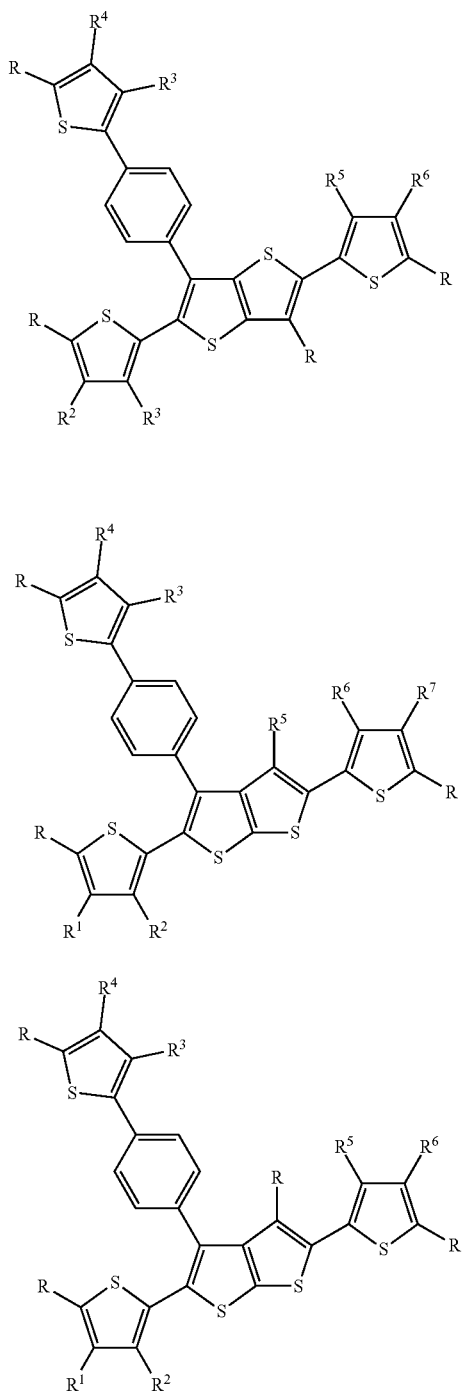
and wherein R is selected from a group consisting of:
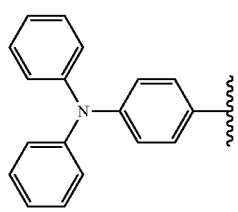
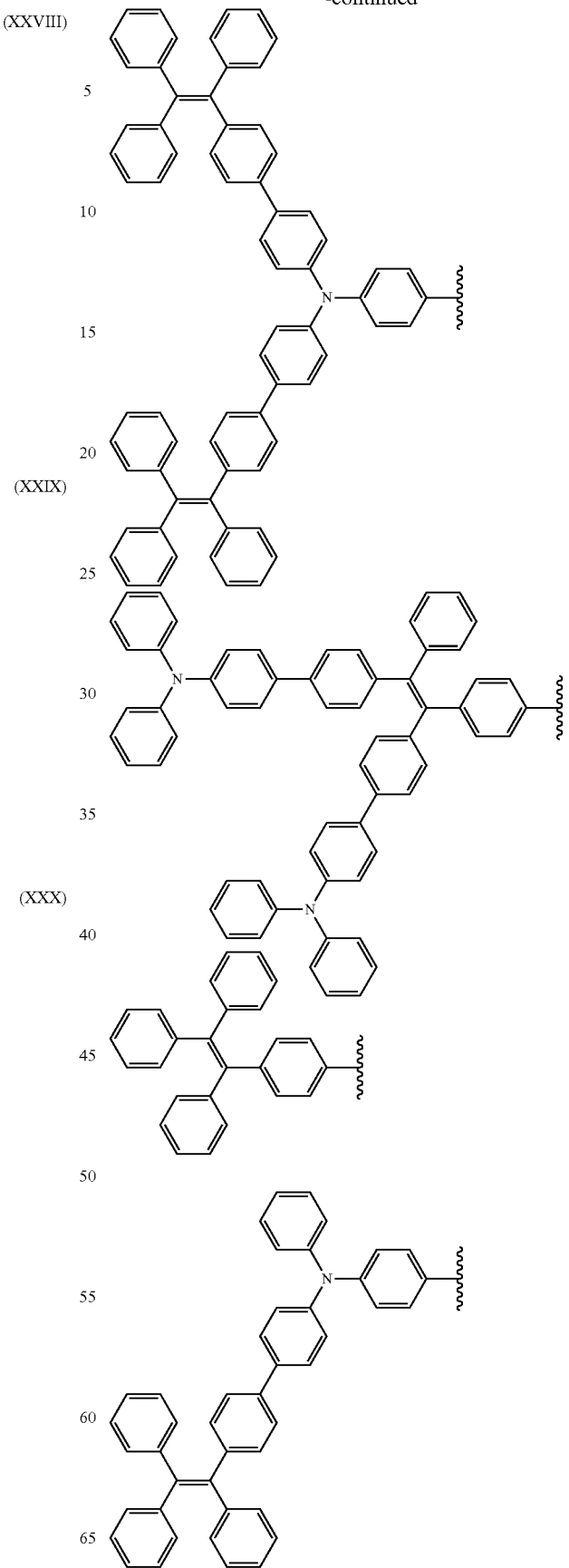

-continued

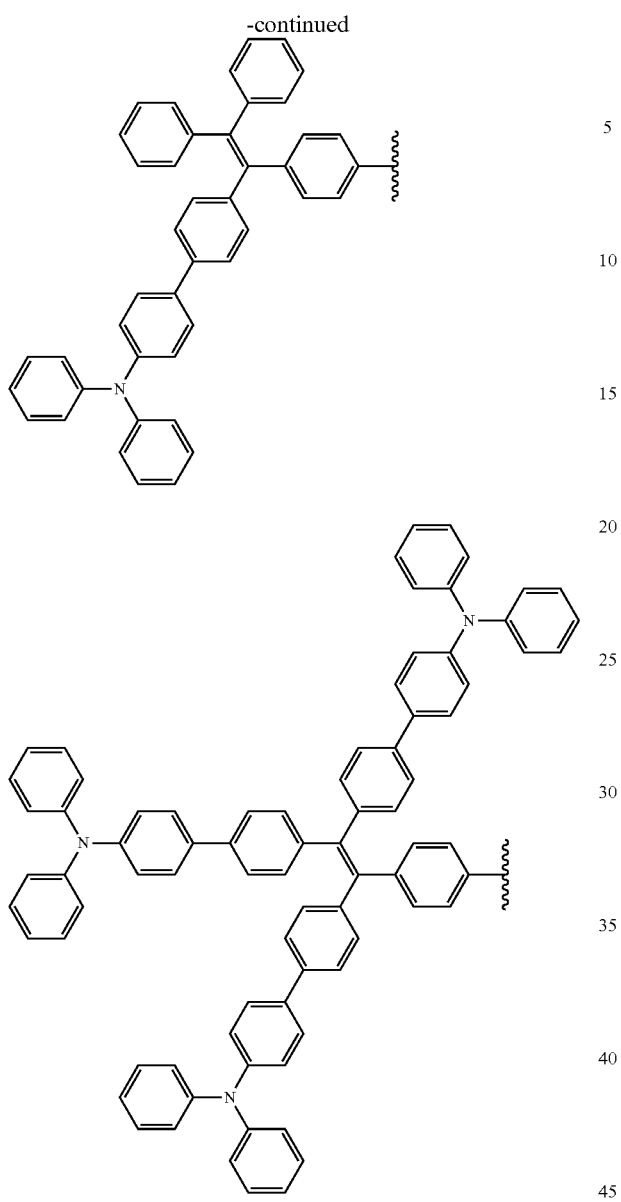

and

R¹, R², R³, R⁴, R⁵, R⁶ and R⁷ are atom chain(s)/group(s) of 1 atom to 100 atoms and wherein R¹, R², R³, R⁴, R⁵, R⁶ and R⁷ comprise at least one of an alkyl, aryl, alkenyl, alkynyl, amine, ester, carbonate ester, carbonyl, sulphide, organosilane or thiolate group.

6. A blend comprising one or more compounds disclosed in claim 5.

7. A formulation comprising one or more compounds disclosed in claim 5.

8. A blend or formulation comprising one or more compounds disclosed in claim 5, wherein the blend or formulation is used in at least one of charge transport, electrically conducting, semiconducting, photoconducting or light emitting materials in electronic, optical, electrooptical, electroluminescent or photoluminescent devices.

9. A polymer or small molecule comprising one or more formulas selected from a group of formulas (XXXI), (XXXII), (XXXIII), (XXXIV), (XXXV), (XXXVI), (XXXVII), (XXXVIII), (XXXIX), (XL), (XLI), (XLII), (XLIII), (XLIV), (XLV), (XLVI), (XVLVII), (XLVIII), (XLIX) and (L) as follows:

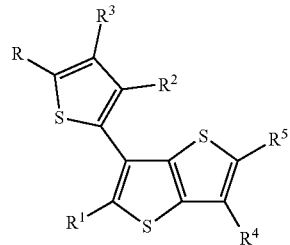

(XXXI)

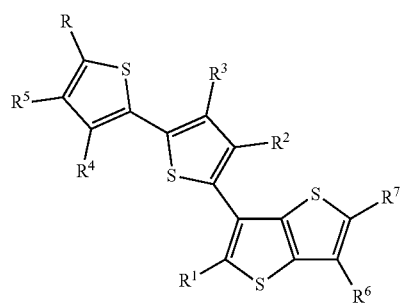

(XXXII)

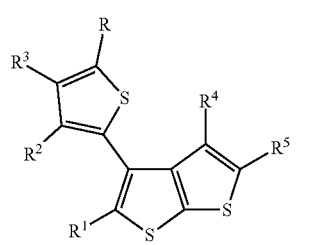

(XXXIII)

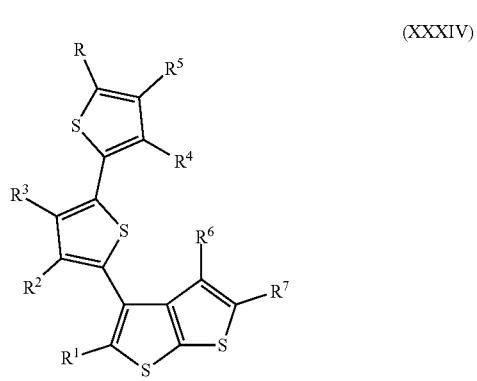

(XXXIV)

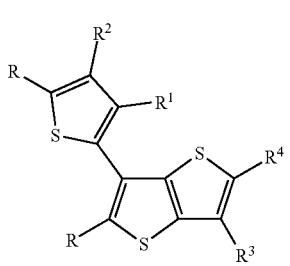

(XXXV)

-continued
(XXXVI)
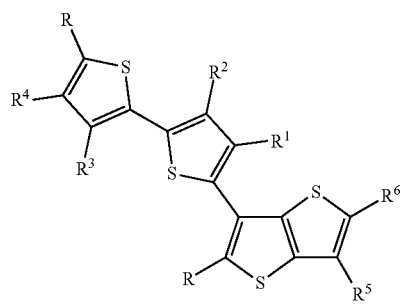
(XXXVII)
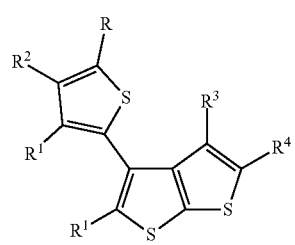
(XXXVIII)
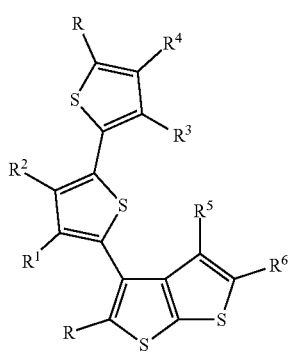
(XXXIX)
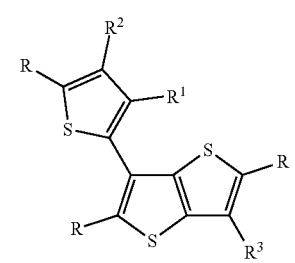
(XL)
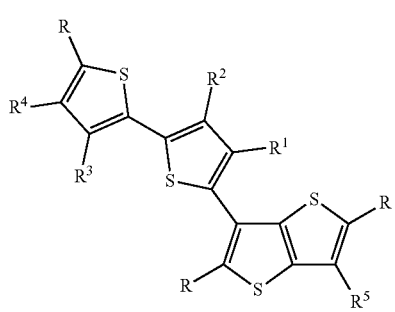
(XLI)
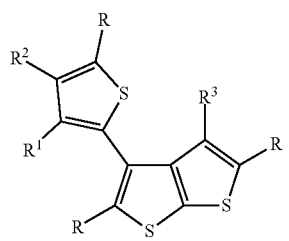
(XLII)
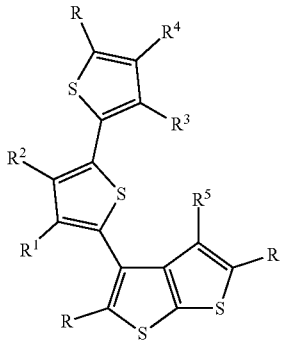
(XLIII)
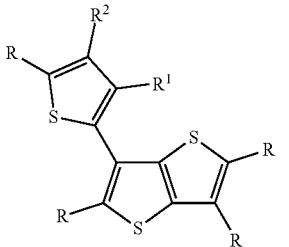
(XLIV)
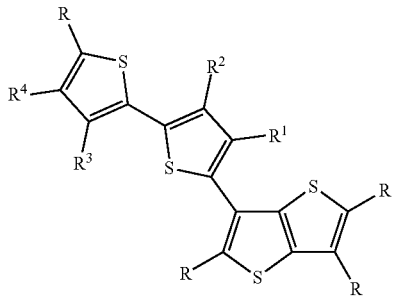
(XLV)
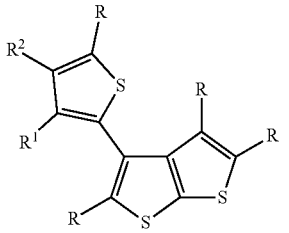

(XLVI)
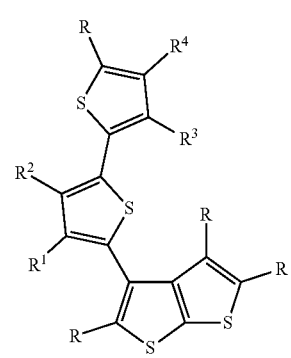
(XLVII)
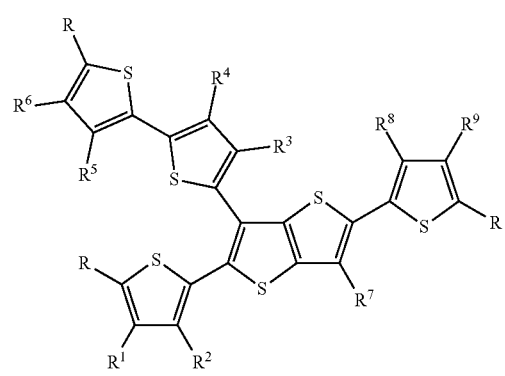
(XLVIII)
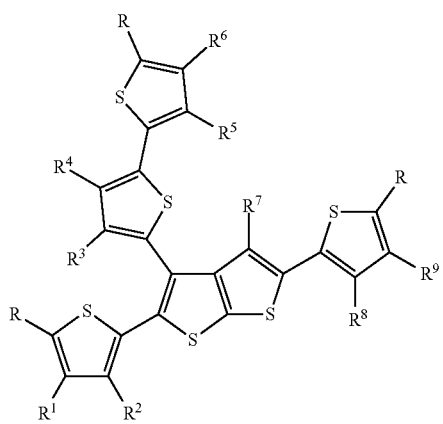
(XLIX)
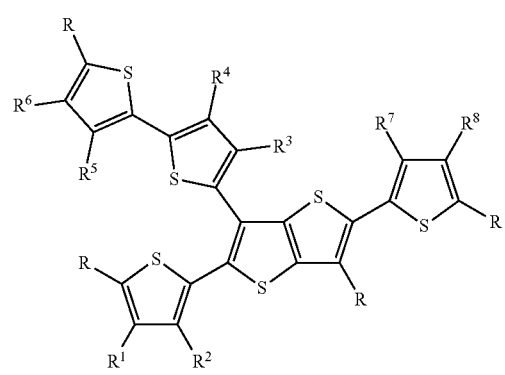
(L)
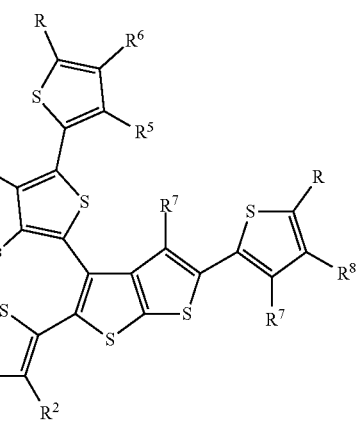
wherein R is selected from a group consisting of:
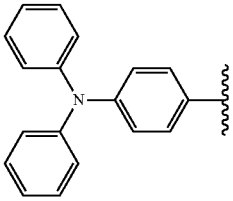
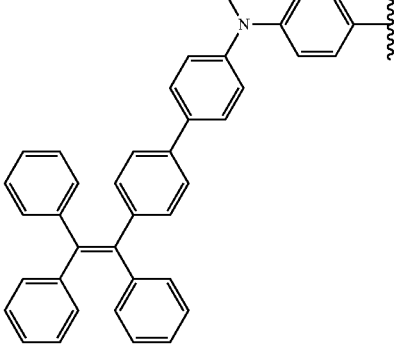

-continued

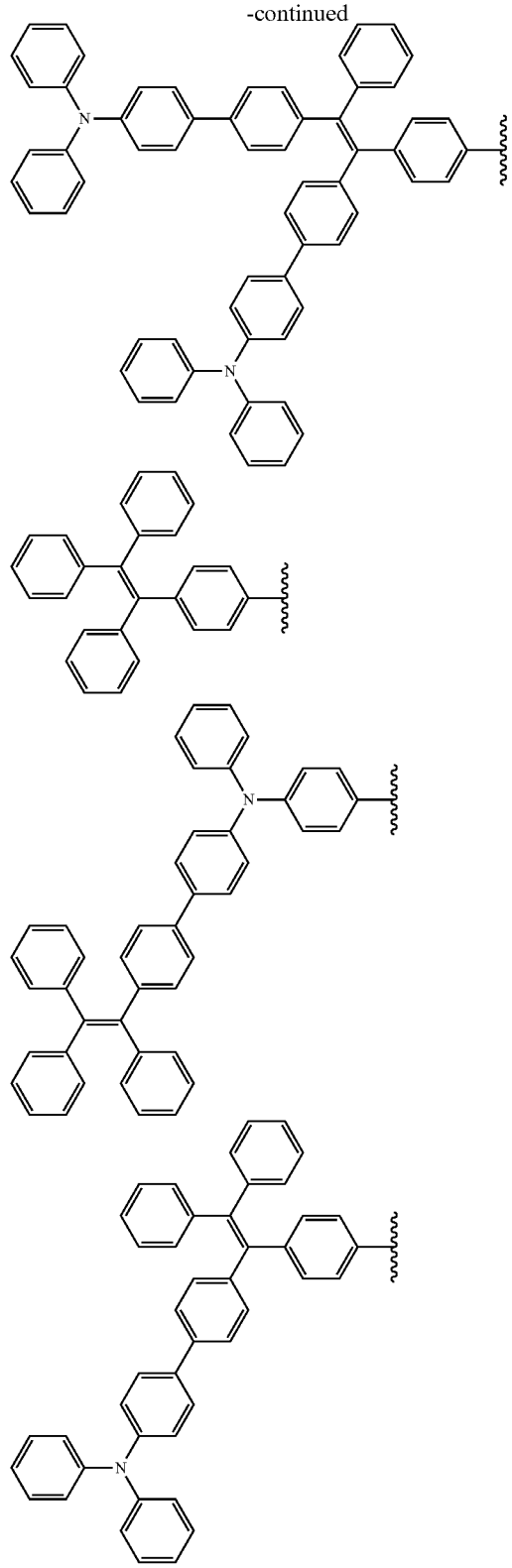

-continued

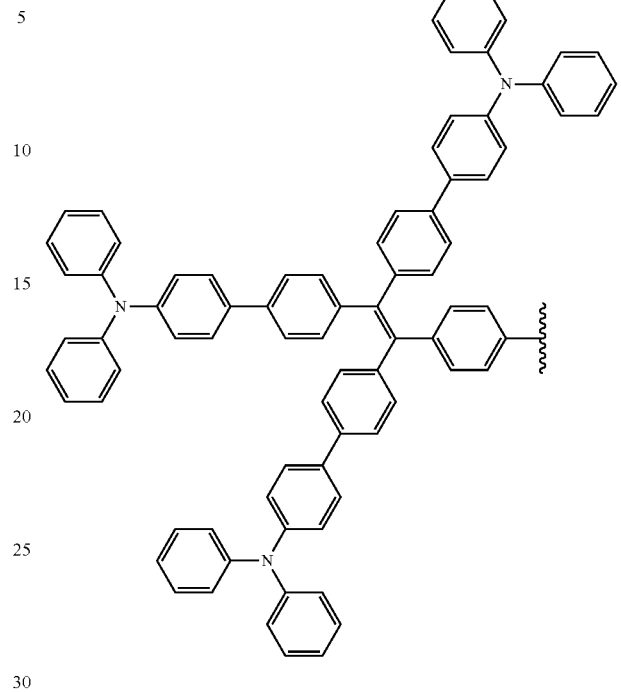

and $R^1$, $R^2$, $R^3$, $R^4$, $R^5$, $R^6$, $R^7$, $R^8$ and $R^9$ are atom chain(s)/group(s) of 1 atom to 100 atoms and wherein R', $R^2$, $R^3$, $R^4$, $R^5$, $R^6$, $R^7$, $R^8$ and $R^9$ comprise at least one of an alkyl, aryl, alkenyl, alkynyl, amine, ester, carbonate ester, carbonyl, sulphide, organosilane or thiolate group.

10. A blend comprising one or more compounds disclosed in claim 9.

11. A formulation comprising one or more compounds given in claim 9.

12. A blend or formulation comprising one or more compounds disclosed in claim 9, wherein the blend or formulation is used in at least one of charge transport, electrically conducting, semiconducting, photoconducting or light emitting materials in electronic, optical, electrooptical, electroluminescent or photoluminescent devices.

13. The polymer or small molecule of claim 1, wherein the polymer or small molecule is a thienotheiophene.

14. The polymer or small molecule of claim 5, wherein the polymer or small molecule is a thienotheiophene.

15. The polymer or small molecule of claim 9, wherein the polymer or small molecule is a thienotheiophene.

* * * * *